(12) United States Patent
Pacetti et al.

(10) Patent No.: US 9,675,478 B2
(45) Date of Patent: Jun. 13, 2017

(54) SOLVENT METHOD FOR FORMING A POLYMER SCAFFOLDING

(71) Applicant: Abbott Cardiovascular Systems Inc., Santa Clara, CA (US)

(72) Inventors: Stephen D. Pacetti, San Jose, CA (US); Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 213 days.

(21) Appl. No.: 14/302,295

(22) Filed: Jun. 11, 2014

(65) Prior Publication Data

US 2015/0359647 A1    Dec. 17, 2015

(51) Int. Cl.
*A61F 2/91*    (2013.01)
*A61F 2/82*    (2013.01)
*A61F 2/90*    (2013.01)
*A61L 31/06*   (2006.01)

(52) U.S. Cl.
CPC ............. *A61F 2/90* (2013.01); *A61L 31/06* (2013.01)

(58) Field of Classification Search
CPC .................................... A61F 2/91; A61F 2/82
USPC ................... 427/2.1, 2.24, 2.25, 337, 372.2; 623/1.15, 1.16
See application file for complete search history.

(56) References Cited

U.S. PATENT DOCUMENTS

| | | | |
|---|---|---|---|
| 2,037,197 A | 4/1936 | Huston | |
| 2,461,372 A | 2/1949 | Collins | |
| 2,752,328 A | 6/1956 | Magat | |
| 2,958,364 A | 11/1960 | Thompson | |
| 3,383,257 A | 5/1968 | James | |
| 3,423,491 A | 1/1969 | McLain et al. | |
| 4,267,215 A | 5/1981 | Riggs | |
| 5,287,632 A * | 2/1994 | Heit ..................... | A61K 9/0004 34/341 |
| 5,403,897 A | 4/1995 | Ebato et al. | |
| 5,417,981 A | 5/1995 | Endo et al. | |
| 5,490,962 A | 2/1996 | Cima et al. | |
| 5,637,113 A * | 6/1997 | Tartaglia ................... | A61F 2/07 604/104 |
| 5,707,329 A | 1/1998 | Free et al. | |
| 5,980,972 A | 11/1999 | Ding | |
| 5,981,694 A | 11/1999 | Gruber et al. | |
| 6,350,009 B1 | 2/2002 | Freund et al. | |
| 6,547,994 B1 | 4/2003 | Monkhouse et al. | |
| 7,112,298 B2 | 9/2006 | Kampa et al. | |
| 7,163,715 B1 | 1/2007 | Kramer | |
| 7,201,940 B1 | 4/2007 | Kramer | |
| 7,229,471 B2 | 6/2007 | Gale et al. | |
| 7,517,353 B2 | 4/2009 | Weber | |
| 7,591,831 B2 | 9/2009 | Parsonage et al. | |
| 7,622,070 B2 | 11/2009 | Atladottir et al. | |
| 7,704,544 B2 | 4/2010 | Pacetti et al. | |

(Continued)

OTHER PUBLICATIONS

Cryogenic Grinding, http://en.wikipedia.org/wiki/Cryogenic_grinding, printed Sep. 17, 2014, 2 pages.

(Continued)

*Primary Examiner* — Cachet Sellman
(74) *Attorney, Agent, or Firm* — Squire Patton Boggs (US) LLP

(57) ABSTRACT

Methods of making polymeric devices, such as stents, using solvent based processes. More particularly, methods of making bioabsorbable stents.

21 Claims, 2 Drawing Sheets

(56) References Cited

U.S. PATENT DOCUMENTS

| | | | |
|---|---|---|---|
| 8,089,029 B2 | 1/2012 | Flanagan | |
| 8,221,822 B2 | 7/2012 | Flanagan et al. | |
| 8,281,737 B2 | 10/2012 | Austin et al. | |
| 8,481,138 B2 | 7/2013 | Miller et al. | |
| 8,524,148 B2 | 9/2013 | Shrivastava et al. | |
| 8,529,719 B2 | 9/2013 | Pingleton et al. | |
| 8,563,103 B2 | 10/2013 | Hammann et al. | |
| 2004/0098100 A1 | 5/2004 | Williams et al. | |
| 2007/0154512 A1* | 7/2007 | Dave | A61K 9/0024 424/423 |
| 2007/0179219 A1 | 8/2007 | Huang et al. | |
| 2007/0212547 A1 | 9/2007 | Fredrickson et al. | |
| 2007/0233277 A1* | 10/2007 | Yamamoto | A61B 17/1128 623/23.75 |
| 2008/0100685 A1* | 5/2008 | Otis | B05D 1/26 347/100 |
| 2008/0103584 A1 | 5/2008 | Su et al. | |
| 2009/0156772 A1 | 6/2009 | Strickler et al. | |
| 2009/0319028 A1 | 12/2009 | Ramzipoor et al. | |
| 2010/0004734 A1* | 1/2010 | Ramzipoor | A61F 2/91 623/1.15 |
| 2010/0096781 A1 | 4/2010 | Huang et al. | |
| 2010/0104734 A1* | 4/2010 | Orosa | A61L 31/10 427/2.25 |
| 2010/0262224 A1* | 10/2010 | Kleiner | A61L 31/06 623/1.15 |
| 2012/0282392 A1 | 11/2012 | Sun | |
| 2013/0041129 A1 | 2/2013 | Steichen et al. | |
| 2013/0115466 A1 | 5/2013 | Madsen et al. | |
| 2013/0150943 A1 | 6/2013 | Zheng et al. | |
| 2013/0216421 A1 | 8/2013 | Buckman, Jr. et al. | |
| 2013/0289690 A1* | 10/2013 | Thapliyal | A61F 2/844 623/1.2 |
| 2013/0331927 A1 | 12/2013 | Zheng et al. | |
| 2014/0011929 A1 | 1/2014 | Knoll et al. | |
| 2015/0359947 A1 | 12/2015 | Hossainy et al. | |

OTHER PUBLICATIONS

Molar Mass Distribution, http://en.wikipedia.org/wiki/Molar_mass_distribution, printed May 16, 2014, 4 pages.

Sintering, http://en.wikipedia.org/wiki/Sintering, printed May 21, 2014, 15 pages.

Viscosity, http://en.wikipedia.org/wiki/Viscosity, printed Jun. 6, 2014, 24 pages.

International Search Report and Written Opinion of the International Searching Authority mailed on Nov. 9, 2015, for International Patent Application No. PCT/US2015/035171, 25 pp.

Non-Final Rejection in U.S. Appl. No. 14/304,792, mailed on Jul. 31, 2015; 9 pages.

Notice of Allowance in U.S. Appl. No. 14/304,792, mailed on Nov. 12, 2015; 5 pages.

Supplemental Notice of Allowability in U.S. Appl. No. 14/304,792, mailed on Jun. 9, 2016; 2 pages.

\* cited by examiner

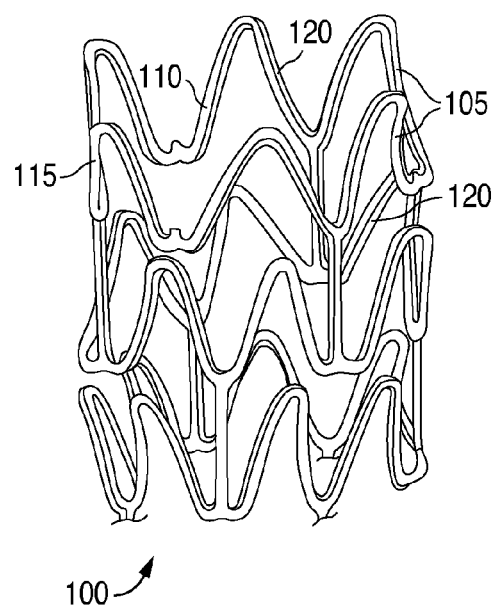
FIG. 1
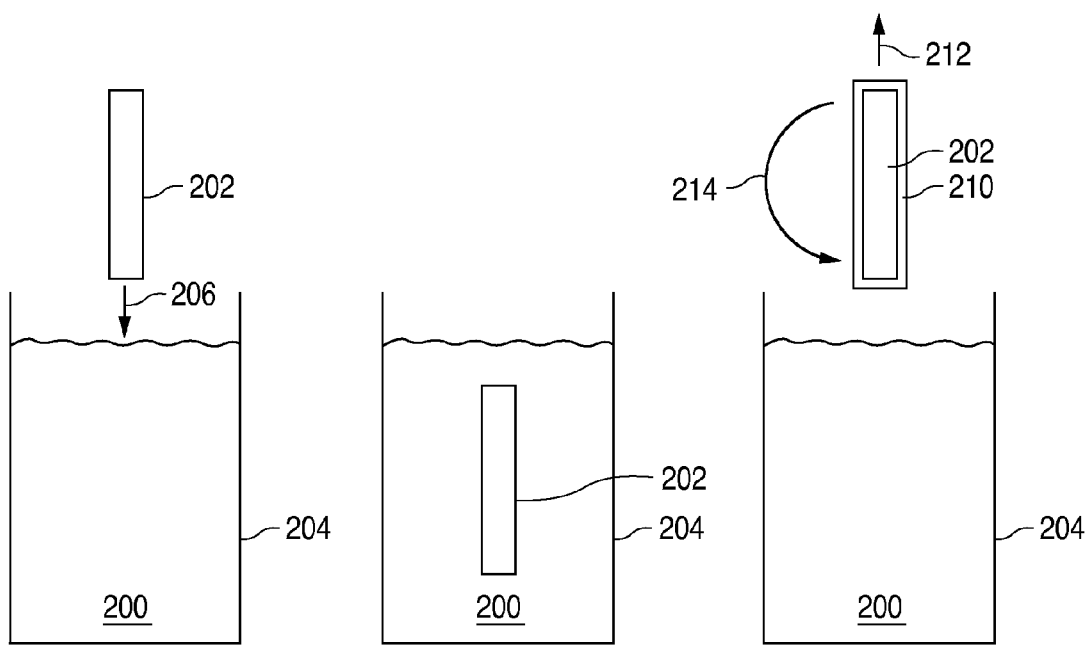
FIG. 2A  FIG. 2B  FIG. 2C

SOLVENT METHOD FOR FORMING A POLYMER SCAFFOLDING

BACKGROUND

Field of the Invention

This invention relates to methods of manufacturing polymeric medical devices, in particular, bioabsorbable medical devices, and especially stents used in the treatment of blood vessels.

Description of the State of the Art

Until the mid-1980s, the accepted treatment for atherosclerosis, i.e., narrowing of the coronary artery(ies) was by-pass surgery. While effective and evolved to a relatively high degree of safety for such an invasive procedure, by-pass surgery still involves potentially serious complications, and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a relatively short time compared to by-pass surgery, and the recovery time was minimal. However, PTCA brought with it other problems such as vasospasm and elastic recoil of the stretched arterial wall which could undo much of what was accomplished and, in addition, it created a new disease, restenosis, the re-clogging of the treated artery due to neointimal hyperplasia.

The next improvement, advanced in the mid-1980s, was the use of a stent to maintain the luminal diameter after PTCA. This for all intents and purposes put an end to vasospasm and elastic recoil, but did not entirely resolve the issue of restenosis. That is, prior to the introduction of stents restenosis occurred in about 30-50% of patients undergoing PTCA. Stenting reduced this to about 15-20%, much improved but still more than desirable.

In 2003, drug-eluting stents or DESs were introduced. The drugs initially employed with the DES were cytostatic and cytotoxic compounds, that is, compounds that curtailed the proliferation of cells that contributed to restenosis. The occurrence of restenosis was thereby reduced to about 5-7%, a relatively acceptable figure. Thus, stents made from biostable or non-erodible materials, such as metals, have become the standard of care for percutaneous coronary intervention (PCI) as well as in peripheral applications, such as the superficial femoral artery (SFA), since such stents have been shown to be capable of preventing early and later recoil and restenosis.

However, a problem that arose with the advent of DESs was so-called "late stent thrombosis," the forming of blood clots long after the stent was in place. It was hypothesized that the formation of blood clots was most likely due to delayed healing, a side-effect of the use of cytostatic and cytotoxic drugs. One potential solution is to make a stent from materials that erode or disintegrate through exposure to conditions within the body. Thus, erodible portions of the stent can disappear from the implant region after the treatment is completed, leaving a healed vessel. Stents fabricated from biodegradable, bioabsorbable, and/or bioerodable materials such as polymers can be designed to completely erode only after the clinical need for them has ended. Like a durable stent, a biodegradable stent must meet time dependent mechanical requirements. For example, it must provide patency for a minimum time period.

Thus, there is a continuing need for stents, particularly bioabsorbable stents, that meet both mechanical requirements, and methods of forming such stents.

SUMMARY OF THE INVENTION

Embodiments of the present invention include the following, without limitation, as described in the following numbered paragraphs:

[0001] A method of making a stent body for supporting a vascular lumen, including, but not limited to, providing or forming a polymer solution comprising a solvent and a polymer with an inherent viscosity of at least 3.3 dl/g, a number average molecular weight greater than 250,000 g/mole as measured by gel permeation chromatography using polystyrene standards, or both; and either (a) immersing a cylindrical member into the polymer solution and removing the cylindrical member from the polymer solution; wherein a portion of the polymer solution remains on the surface of the cylindrical member upon removal from the polymer solution; and removing at least a portion of the solvent from the polymer solution remaining on the cylindrical member to form a tubular layer of the polymer on the cylindrical member; or (b) spraying the polymer solution onto the cylindrical member; and removing the solvent during, after, or both during and after the spraying to form a tubular layer of the polymer on the cylindrical member; optionally, repeating (a) on one or more occasions, repeating (b) on one or more occasions, or both, with repeating of the providing or forming prior to repeating (a), (b), or both, being optional (because the previous solution may be used for the repetition), to form a final tubular layer of polymer on the cylindrical member of a desired thickness; removing residual solvent from the final tubular layer; and forming a stent body from the final tubular layer. With respect to the above method, if the optional providing or forming of the polymer solution is repeated, for each repetition of the providing or forming, the solvent, the polymer, or both, of the polymer solution may be different from the polymer, the solvent, or both used in the prior execution of (a), (b), or both. In addition, with respect to the above method, removal of the residual solvent of the polymer solution from the final tubular layer comprises at least one of the following: removal in a humid environment of 25% to 100% rh: removal in an environment of solvent vapor, the solvent being the removal solvent, where the removal solvent may the same as or different from the solvent of the polymer solution; removal by exposure to a supercritical fluid; removal by freeze drying.

[0002] In some embodiments, such as but not limited to that described in paragraph [0001], a residual solvent level of less than 2500 ppm (parts per million by weight) is achieved prior to coating the stent, packaging the stent, or both, or a residual solvent level of less than 1000 ppm is achieved prior to coating the stent, packaging the stent, or both.

[0003] In some embodiments, such as but not limited to that described in paragraph [0001], a residual solvent level of less than 100 ppm is achieved prior to coating the stent, packaging the stent, or both, or a residual solvent level of less than 25 ppm is achieved prior to coating the stent, packaging the stent, or both.

[0004] In some embodiments, such as but not limited to those described in paragraphs [0001]-[0003], at least a portion of the solvent removal occurs during further processing of the final tubular layer before the formation of the stent from the final tubular layer, after further processing before the formation of the stent from the final tubular layer, or both.

[0005] In some embodiments, such as but not limited to those described in paragraphs [0001]-[0004], at least a portion of the solvent removal occurs after the formation of the stent from the final tubular layer.

[0006] In some embodiments, such as but not limited to those described in paragraphs [0001]-[0005], (a) is executed at least once and (b) is executed at least once.

[0007] In some embodiments, such as but not limited to those described in paragraphs [0001]-[0005], (a) is executed at least once.

[0008] In some embodiments, such as but not limited to those described in paragraph [0007], (a) is executed at least twice.

[0009] In some embodiments, such as but not limited to those described in paragraph [0008], (a) is executed at least 5 times.

[0010] In some embodiments, such as but not limited to those described in paragraphs [0001]-[0005], wherein (b) is executed at least once.

[0011] In some embodiments, such as but not limited to those described in paragraph [0010], (b) is executed at least twice.

[0012] In some embodiments, such as but not limited to those described in paragraph [0011], (b) is executed at least 5 times.

[0013] In some embodiments, such as but not limited to those described in paragraphs [0001]-[0012], residual solvent removal comprises removal in a humid environment where the humid environment is of 25% to 100% relative humidity (rh).

[0014] In some embodiments, such as but not limited to those described in paragraph [0013], the humid environment is of 40% to 100% rh.

[0015] In some embodiments, such as but not limited to those described in paragraph [0013], the humid environment is of 65% to 100% rh.

[0016] In some embodiments, such as but not limited to those described in paragraph [0013], the humid environment is of 80% to 100% rh.

[0017] In some embodiments, such as but not limited to those described in paragraphs [0013]-[0016], the removal of residual solvent comprises placing the final tubular layer in the humid environment for a duration of at least 10 minutes and not more than 1,000 hours.

[0018] In some embodiments, such as but not limited to those described in paragraph [0017], the duration is at least 10 minutes and not more than 2 hours.

[0019] In some embodiments, such as but not limited to those described in paragraph [0017], the duration is at least 30 minutes and not more than 4 hours.

[0020] In some embodiments, such as but not limited to those described in paragraph [0017], the duration is at least 1 hour to and not more than 10 hours.

[0021] In some embodiments, such as but not limited to those described in paragraph [0017], the duration is at least 1 hour and not more than 12 hours.

[0022] In some embodiments, such as but not limited to those described in paragraph [0017], the duration is at least 2 hours and not more than 16 hours.

[0023] In some embodiments, such as but not limited to those described in paragraph [0017], the duration is at least 2 hours and not more than 24 hours.

[0024] In some embodiments, such as but not limited to those described in paragraph [0017], the duration is at least 4 hours and not more than 48 hours.

[0025] In some embodiments, such as but not limited to those described in paragraph [0017], the duration is at least 12 hours and not more than 72 hours.

[0026] In some embodiments, such as but not limited to those described in paragraph [0017], the duration is at least 24 hours and not more than 200 hours.

[0027] In some embodiments, such as but not limited to those described in paragraph [0017], the duration is at least 0.2 hours and not more than 1,000 hours.

[0028] In some embodiments, such as but not limited to those described in paragraph [0017], the duration is at least 0.5 hours and not more than 1,000 hours.

[0029] In some embodiments, such as but not limited to those described in paragraph [0017], the duration is at least 1 hour and not more than 1,000 hours.

[0030] In some embodiments, such as but not limited to those described in paragraphs [0013]-[0029], the temperature of the humid environment, the temperature to which the polymer is heated to and maintained at in the humid environment, or both, is a temperature not less than 30° C., but not more than the glass transition temperature of the polymer if the polymer has a glass transition temperature of greater than 30° C.

[0031] In some embodiments, such as but not limited to those described in paragraphs [0013]-[0029], the temperature of the humid environment, the temperature to which the polymer is heated to and maintained at in the humid environment, or both, is a temperature not less than the glass transition temperature of the polymer, or a temperature of not less than 28° C., if the glass transition temperature is lower than 25° C., and not more than the melting temperature of the polymer, if the polymer has a melting temperature that is not less than 45° C., or not more than 50° C. above the glass transition temperature of the polymer, if the polymer does not have a melting temperature that is not less than 45° C., or not more than 45° C., if 50° C. above the glass transition temperature of the polymer is less than 45° C., the melting temperature is less than 45° C., or both.

[0032] In some embodiments, such as but not limited to those described in paragraph [0031], the temperature of the humid environment, the temperature to which the polymer is heated to and maintained at in the humid environment, or both, is a temperature of at least 30° C.

[0033] In some embodiments, such as but not limited to those described in paragraph [0031], the temperature of the humid environment, the temperature to which the polymer is heated to and maintained at in the humid environment, or both, is a temperature of at least 32° C.

[0034] In some embodiments, such as but not limited to those described in paragraph [0031], the temperature of the humid environment, the temperature to which the polymer is heated to and maintained at in the humid environment, or both, is a temperature of at least 32° C., or at least 10° C. above the glass transition temperature, whichever is higher, and not more than 10° C. below the melting temperature, if the polymer has a melting temperature that is at least 45° C. and is greater than 10° C. above the glass transition temperature, or not more than the higher of 40° C. above the glass transition temperature and 45° C.

[0035] In some embodiments, such as but not limited to those described in paragraphs [0013]-[0029], provided that the glass transition temperature is not less than 25° C., the temperature of the humid environment, the temperature to which the polymer is heated to and maintained at in the humid environment, or both, is a temperature between 15° C. above the glass transition temperature and 15° C. below the melting temperature, if the polymer has a melting temperature of at least 60° C. and there is more than 30° C. between the glass transition temperature and the melting temperature, or if the polymer has no melting temperature of at least 60° C., between 10° C. and 45° C. above the glass transition temperature, or between 15° C. and 40° C. above the glass transition temperature.

[0036] In some embodiments, such as but not limited to those described in paragraphs [0013]-[0035], the humid environment is at a pressure of 760 Torr±100 Torr.

[0037] In some embodiments, such as but not limited to those described in paragraphs [0013]-[0035], the humid environment is at a pressure of 760 Torr±50 Torr.

[0038] In some embodiments, such as but not limited to those described in paragraphs [0013]-[0035], the humid environment is at a pressure of not more than 380 Torr, but at least 0.001 Torr.

[0039] In some embodiments, such as but not limited to those described in paragraphs [0013]-[0035], the humid environment is at a pressure of not more than 200 Torr, but at least 0.001 Torr.

[0040] In some embodiments, such as but not limited to those described in paragraphs [0013]-[0039], at least a portion of water absorbed by the polymer is removed from the polymer after the removal of the residual solvent.

[0041] In some embodiments, such as but not limited to those described in paragraph [0040], removal of any absorbed water comprises placing the polymer in an low humidity environment where the humidity is equal to or less than 40% rh, and at least 0.001% rh.

[0042] In some embodiments, such as but not limited to those described in paragraph [0041], the humidity of the low humidity environment is equal to or less than 30% rh.

[0043] In some embodiments, such as but not limited to those described in paragraph [0041], the humidity of the low humidity environment is equal to or less than 20% rh.

[0044] In some embodiments, such as but not limited to those described in paragraphs [0001]-[0012], residual solvent removal comprises removal in an environment of removal solvent vapor, where the removal solvent may be the same as or different from the solvent of the polymer solution.

[0045] In some embodiments, such as but not limited to those described in paragraph [0044], the removal solvent is different from the solvent of the polymer solution.

[0046] In some embodiments, such as but not limited to those described in paragraphs [0044] and [0045], the removal solvent plasticizes the polymer.

[0047] In some embodiments, such as but not limited to those described in paragraphs [0044]-[0046], the removal solvent has a boiling point of less than or equal to 80° C.

[0048] In some embodiments, such as but not limited to those described in paragraph [0047], the removal solvent has a boiling point of less than or equal to 60° C.

[0049] In some embodiments, such as but not limited to those described in paragraphs [0044]-[0046], the removal solvent is selected from the group consisting of acetonitrile, methanol, ethanol, n-propanol, isopropanol, butanol, fluoroform, freons, methylene chloride ($CH_2Cl_2$), and chloroform ($CHCl_3$), and freons.

[0050] In some embodiments, such as but not limited to those described in paragraphs [0044]-[0048], the removal solvent partial pressure is at least 100 Torr.

[0051] In some embodiments, such as but not limited to those described in paragraphs [0044]-[0049], the removal solvent partial pressure is between 30 Torr and 500 Torr.

[0052] In some embodiments, such as but not limited to those described in paragraphs [0044]-[0051], the removal solvent partial pressure is at least 25% of the value of the pure removal solvent vapor pressure at the temperature of the environment.

[0053] In some embodiments, such as but not limited to those described in paragraphs [0044]-[0052], the removal solvent partial pressure is at least 50% of the value of the pure removal solvent vapor pressure at the temperature of the environment.

[0054] In some embodiments, such as but not limited to those described in paragraphs [0044]-[0053], the removal solvent partial pressure is at least 75% of the value of the pure removal solvent vapor pressure at the temperature of the environment.

[0055] In some embodiments, such as but not limited to those described in paragraphs [0044]-[0054], the removal solvent partial pressure is at least 90% of the value of the pure removal solvent vapor pressure at the temperature of the environment.

[0056] In some embodiments, such as but not limited to those described in paragraphs [0044]-[0055], the removal of residual solvent of the polymer solution in an environment of removal solvent vapor comprises placing the final tubular layer in an environment of removal solvent vapor for a duration of at least 10 minutes and not more than 1,000 hours.

[0057] In some embodiments, such as but not limited to those described in paragraph [0056], the duration is least 10 minutes and not more than 2 hours.

[0058] In some embodiments, such as but not limited to those described in paragraph [0056], the duration is at least 30 minutes and not more than 4 hours.

[0059] In some embodiments, such as but not limited to those described in paragraph [0056], the duration is least 1 hour to and not more than 10 hours.

[0060] In some embodiments, such as but not limited to those described in paragraph [0056], the duration is at least 1 hour and not more than 12 hours.

[0061] In some embodiments, such as but not limited to those described in paragraph [0056], the duration is at least 2 hours and not more than 16 hours.

[0062] In some embodiments, such as but not limited to those described in paragraph [0056], the duration is at least 2 hours and not more than 24 hours.

[0063] In some embodiments, such as but not limited to those described in paragraph [0056], the duration is at least 4 hours and not more than 48 hours.

[0064] In some embodiments, such as but not limited to those described in paragraph [0056], the duration is at least 12 hours and not more than 72 hours.

[0065] In some embodiments, such as but not limited to those described in paragraph [0056], the duration is at least 24 hours and not more than 200 hours.

[0066] In some embodiments, such as but not limited to those described in paragraph [0056], the duration is at least 0.2 hours and not more than 1,000 hours.

[0067] In some embodiments, such as but not limited to those described in paragraph [0056], the duration is at least 0.5 hours and not more than 1,000 hours.

[0068] In some embodiments, such as but not limited to those described in paragraph [0056], the duration is at least 1 hour and not more than 1,000 hours.

[0069] In some embodiments, such as but not limited to those described in paragraphs [0044]-[0068], the temperature of the environment of removal solvent vapor, the temperature to which the polymer is heated to and maintained at in the environment of removal solvent vapor, or both, is not less than 30° C. but not more than the glass transition temperature of the polymer, provided the polymer has a glass transition temperature of at least 30° C.

[0070] In some embodiments, such as but not limited to those described in paragraphs [0044]-[0068], the temperature of the environment of removal solvent vapor, the temperature to which the polymer is heated to and maintained at in the environment of removal solvent vapor, or both, is not less than the glass transition temperature of the polymer, or not less than 28° C., if the glass transition temperature is lower than 25° C., and not more than the melting temperature of the polymer, if the polymer has a melting temperature of at least 45° C., or not more than the higher of 50° C. above the glass transition temperature of the polymer and 45° C.

[0071] In some embodiments, such as but not limited to those described in paragraphs [0044]-[0068], the temperature of the environment of removal solvent vapor, the temperature to which the polymer is heated to and maintained at in the environment of removal solvent vapor, or both, is not less than 32° C. but not more than the glass transition temperature of the polymer, provided the glass transition temperature is at least 32.5° C.

[0072] In some embodiments, such as but not limited to those described in paragraphs [0044]-[0068], the temperature of the environment of removal solvent vapor, the temperature to which the polymer is heated to and maintained at in the environment of removal solvent vapor, or both, is not less than the glass transition temperature of the polymer, or not less than 28° C., if the glass transition temperature is lower than 25° C., and not more than the melting temperature of the polymer, if the polymer has a melting temperature of at least 55° C., or not more than the higher of 60° C. above the glass transition temperature of the polymer, and 55° C.

[0073] In some embodiments, such as but not limited to those described in paragraphs [0044]-[0072], the temperature of the environment of removal solvent vapor, the temperature to which the polymer is heated to and maintained at in the environment of removal solvent vapor, or both, is at least 30° C.

[0074] In some embodiments, such as but not limited to those described in paragraphs [0044]-[0072], the temperature of the environment of removal solvent vapor, the temperature to which the polymer is heated to and maintained at in the environment of removal solvent vapor, or both, is at least 32° C.

[0075] In some embodiments, such as but not limited to those described in paragraphs [0044]-[0068], the temperature of the environment of removal solvent vapor, the temperature to which the polymer is heated to and maintained at in the environment of removal solvent vapor, or both, is at least 32° C., or at least 10° C. above the glass transition temperature, whichever is higher, and not more than 10° C. below the melting temperature, if the polymer has a melting temperature of at least 55° C., or not more than the higher of 40° C. above the glass transition temperature of the polymer, and 45° C.

[0076] In some embodiments, such as but not limited to those described in paragraphs [0044]-[0068], provided that the glass transition temperature is not less than 25° C., the temperature of the environment of removal solvent vapor, the temperature to which the polymer is heated to and maintained at in the environment of removal solvent vapor, or both, is between 15° C. above the glass transition temperature and 15° C. below the melting temperature, if the polymer has a melting temperature of at least 60° C. and there is more than 30° C. between the glass transition temperature and the melting, or if the polymer has no melting temperature or there is less than 30° C. between the glass transition temperature and the melting temperature, between 10° C. and 45° C. above the glass transition temperature, or between 15° C. and 40° C. above the glass transition temperature.

[0077] In some embodiments, such as but not limited to those described in paragraphs [0044]-[0076], the environment of removal solvent vapor is at a pressure of 760 Torr±100 Torr.

[0078] In some embodiments, such as but not limited to those described in paragraphs [0044]-[0076], the environment of removal solvent vapor is at a pressure of 760 Torr±50 Torr.

[0079] In some embodiments, such as but not limited to those described in paragraphs [0044]-[0076], the environment of removal solvent vapor is at a pressure of not more than 380 Torr, but at least 0.001 Torr.

[0080] In some embodiments, such as but not limited to those described in paragraphs [0044]-[0076], the environment of removal solvent vapor is at a pressure of not more than 200 Torr, but at least 0.001 Torr.

[0081] In some embodiments, such as but not limited to those described in paragraphs [0001]-[0012], removal of residual solvent from the polymer solution comprises exposure to a supercritical fluid.

[0082] In some embodiments, such as but not limited to those described in paragraph [0081], the supercritical fluid is carbon dioxide, methane, ethane, or ethylene.

[0083] In some embodiments, such as but not limited to those described in paragraphs [0081] and [0082], the duration of the supercritical exposure ranged from about 5 minutes to about 120 minutes.

[0084] In some embodiments, such as but not limited to those described in paragraphs [0001]-[0012], removal of residual solvent from the polymer solution comprises freeze drying.

[0085] A method of making a stent body for supporting a vascular lumen, including providing or forming a polymer solution including, but not excluding other components, a solvent and a polymer with an inherent viscosity of at least 3.3 dl/g, a number average molecular weight greater than 250,000 g/mole as measured by gel permeation chromatography using polystyrene standards, or both; partially or completely immersing a cylindrical member in the polymer solution comprising the polymer; wherein the cylindrical member is in a horizontal position (cylindrical axis parallel to the polymer solution surface) during at least part of the immersion; removing the cylindrical member from the solution, wherein a portion of the polymer solution remains on the surface of the cylindrical member upon removal from the polymer solution; removing solvent from the polymer solution remaining on the cylindrical member to form a tubular layer of the polymer on the cylindrical member; optionally, repeating the immersion step, removal from the polymer solution step, and removal of the solvent step on one or more occasions (where for each repetition the providing or forming the polymer solution may be optionally repeated) to form a final tubular layer of polymer on the cylindrical member of a desired thickness; and forming a stent body from the final tubular layer. With respect to the method, for the optional repetition of the providing or forming the polymer solution, the solvent and the polymer of the polymer solution may each be the same or different from the polymer, the solvent, or both in the previous polymer solution.

[0086] In some embodiments, such as but not limited to that described in paragraph [0085], removal of solvent comprises exposing the cylindrical member to a flow of a heated fluid, where the fluid may be a gas, a liquid, or a supercritical fluid.

[0087] In some embodiments, such as but not limited to that described in paragraph [0086], the heated fluid is at a temperature not less than 30° C. but not more than the glass transition temperature of the polymer provided the polymer has a glass transition temperature greater than 30° C.

[0088] In some embodiments, such as but not limited to that described in paragraph [0086], the polymer has a glass transition temperature greater than 28° C., the heated fluid is at a temperature not less than the glass transition temperature of the polymer, and not more than the melting temperature of the polymer, if the polymer has a melting temperature not less than 50° C., or not more than the higher of not more than 50° C. above the glass transition temperature of the polymer, and 50° C.

[0089] In some embodiments, such as but not limited to that described in paragraph [0086], the heated fluid is at a temperature in the range of about 30° C. to about 90° C.

[0090] In some embodiments, such as but not limited to that described in paragraph [0086], the heated fluid is at a temperature in the range of about 40° C. to about 90° C.

[0091] In some embodiments, such as but not limited to that described in paragraph [0086], the heated fluid is at a temperature in the range of about 50° C. to about 90° C.

[0092] In some embodiments, such as but not limited to those described in paragraphs [0086]-[0091], the cylindrical member is rotated during at least part of the time it is exposed to the flow of the heated fluid.

[0093] In some embodiments, such as but not limited to that described in paragraphs [0085]-[0092], the cylindrical member is in a horizontal position or a position that deviates by not more than 5° from the horizontal throughout the immersion and removal.

[0094] In some embodiments, such as but not limited to that described in paragraphs [0085]-[0093], the cylindrical member is totally immersed.

[0095] In some embodiments, such as but not limited to that described in paragraphs [0085]-[0093], the cylindrical member is partially immersed.

[0096] In some embodiments, such as but not limited to those described in paragraph [0095], the method includes, but is not limited to, partially immersing the cylindrical member into the polymer solution, and rotating the cylindrical member while partially immersed.

[0097] In some embodiments, such as but not limited to those described in paragraph [0096], the cylindrical member is rotated at least 5° but not more than 360°.

[0098] In some embodiments, such as but not limited to those described in paragraph [0096], the cylindrical member is rotated at least 5° but not more than 275°.

[0099] In some embodiments, such as but not limited to those described in paragraph [0096], the cylindrical member is rotated at least 180° but not more than 180°.

[0100] In some embodiments, such as but not limited to those described in paragraph [0096], the cylindrical member is rotated at least 180° but not more than 360°.

[0101] In some embodiments, such as but not limited to those described in paragraph [0096], the cylindrical member is rotated at least 360° but not more than 720°.

[0102] In some embodiments, such as but not limited to those described in paragraph [0096], the cylindrical member is rotated at least two full rotations but not more than 50.

[0103] In some embodiments, such as but not limited to those described in paragraph [0096], wherein the cylindrical member is rotated at least two full rotations but not more than 20.

[0104] In some embodiments, such as but not limited to those described in paragraph [0096], the cylindrical member is rotated at least two full rotations but not more than 1000.

[0105] A method of making a stent body for supporting a vascular lumen, comprising coating a web with a polymer solution comprising a solvent and a polymer, wherein the polymer has an inherent viscosity greater than 3.3 dl/g, has a weight average molecular weight greater than 500,000 g/mole, or both; removing at least a portion of the solvent from the polymer solution remaining on the web to form a polymer film on the web; separating the polymer film from the web; and wrapping the polymer film around a cylindrical member, subject to the constraint that the edges of the film at least touch each other, and optionally overlap; heating at least part of the polymer film to fuse the polymer film into a polymer tube; removing the polymer tube from the cylindrical member; and forming a stent body from the polymer tube.

[0106] In some embodiments, such as but not limited to that described in paragraph [0105], the wrapping occurs when the polymer film is at a temperature not less than the glass transition temperature of the polymer, or not less than 28° C., if the glass transition temperature is lower than 25° C., and not more than the melting temperature of the polymer, if there is a melting temperature of at least 45° C., or not more than the higher of 45° C. and 50° C. above the glass transition temperature of the polymer.

[0107] In some embodiments, such as but not limited to that described in paragraph [0105], if the polymer has a glass transition temperature of at least 28° C., the wrapping occurs when the polymer film is at a temperature not less than the glass transition temperature of the polymer, and not more than 15° C. above the glass transition temperature of the polymer, or the melting temperature of the polymer, if the polymer exhibits a melting temperature, whichever is lower.

[0108] In some embodiments, such as but not limited to those described in paragraphs [0105]-[0107], the polymer film is wrapped around the cylindrical mandrel such that the edges touch each other but do not overlap.

[0109] In some embodiments, such as but not limited to those described in paragraphs [0105]-[0107], the polymer film is wrapped around the cylindrical mandrel such that the edges overlap by not more than 2%, but at least 0.005% of the surface area of the film.

[0110] In some embodiments, such as but not limited to those described in paragraphs [0105]-[0107], the polymer film is wrapped around the cylindrical mandrel such that the edges overlap by not more than 5%, but at least 0.005% of the surface area of the film.

[0111] In some embodiments, such as but not limited to those described in paragraphs [0105]-[0107], the polymer film is wrapped around the cylindrical member such that the edges overlap by not more than 10%, but at least 0.005% of the surface area of the film.

[0112] In some embodiments, such as but not limited to those described in paragraphs [0105]-[0112], the polymer film is wrapped around the cylindrical member such that the edges overlap by not more than 30%, but at least 0.005% of the surface area of the film.

[0113] In some embodiments, such as but not limited to those described in paragraphs [0105]-[0107], the polymer film is wrapped around the cylindrical member at least 1 full time (360°) but less than 2 full times.

[0115] In some embodiments, such as but not limited to those described in paragraphs [0105]-[0107], the polymer film is wrapped around the cylindrical member at least 1 full time but not more than 4.2 full times.

[0116] In some embodiments, such as but not limited to those described in paragraphs [0105]-[0107], the polymer film is wrapped around the cylindrical member at least 2 times, or at least 4 times, but not more than 100 times.

[0117] In some embodiments, such as but not limited to those described in paragraphs [0105]-[0107], the polymer film is wrapped around the cylindrical member at least 5 times, but not more than 100 times.

[0118] In some embodiments, such as but not limited to those described in paragraphs [0105]-[0107], the polymer film is wrapped around the cylindrical member at least 7 times, but not more than 100 times.

[0119] In some embodiments, such as but not limited to those described in paragraphs [0105]-[0107], the polymer film is wrapped around the cylindrical member at least 10 times, but not more than 100 times.

[0120] In some embodiments, such as but not limited to those described in paragraphs [0105]-[0112], heating at least a region of the polymer film comprises heating the edges of the polymer film and the optional overlapping regions of the polymer film to fuse the polymer film to form the polymer tube.

[0121] In some embodiments, such as but not limited to those described in paragraphs [0105]-[0119], heating at least a region of the polymer film comprises heating all or substantially all of the polymer film to fuse the polymer film to form the polymer tube.

[0122] In some embodiments, such as but not limited to those described in paragraphs [0105]-[0121], prior to wrapping the polymer film around the cylindrical member, the polymer film is heated to at least the glass transition temperature of the polymer or at least 28° C., if the glass transition temperature is lower than 25° C., and not more than the melting temperature of the polymer, if the polymer exhibits a melting temperature of at least 40° C., or the higher of 15° C. above the glass transition temperature of the polymer and 43° C. After wrapping the polymer film, the polymer film is maintained at the temperature for a first duration of time, heated to a higher temperature and maintained at the higher temperature for a second duration of time, or both. The higher temperature is not greater than the melting temperature, if there is a melting temperature and it is at least 60° C., or is not more than the higher of 60° C. above the glass transition temperature of the polymer, or 60° C. The first and second durations of time are at least 5 seconds and not more than 120 minutes.

[0123] In some embodiments, such as but not limited to those described in paragraphs [0105]-[0121], prior to wrapping the polymer film around the cylindrical member, the polymer film is heated to a first temperature; and after wrapping the polymer film, the polymer film is maintained at the first temperature for a first duration of time, heated to a higher temperature and maintained at the higher temperature for a second duration of time, or both; and the first and second durations of time are at least 10 seconds and not more than 120 minutes.

[0124] In some embodiments, such as but not limited to those described in paragraph [0123], the first duration of time is at least 10 seconds.

[0125] In some embodiments, such as but not limited to those described in paragraph [0123], the first duration of time is at least 30 seconds.

[0126] In some embodiments, such as but not limited to those described in paragraph [0123], the first duration of time is at least 60 seconds.

[0127] In some embodiments, such as but not limited to those described in paragraph [0123], the first duration of time is at least 2 minutes.

[0128] In some embodiments, such as but not limited to those described in paragraph [0123], the first duration of time is at least 5 minutes.

[0129] In some embodiments, such as but not limited to those described in paragraphs [0123]-[0128], the first duration is not more than 30 minutes.

[0130] In some embodiments, such as but not limited to those described in paragraphs [0123]-[0129], the second duration of time is at least 10 seconds, and not more than 120 minutes.

[0131] In some embodiments, such as but not limited to those described in paragraph [0130], the second duration of time is at least 5 seconds.

[0132] In some embodiments, such as but not limited to those described in paragraph [0130], the second duration of time is at least 30 seconds.

[0133] In some embodiments, such as but not limited to those described in paragraph [0130], the second duration of time is at least 60 seconds.

[0134] In some embodiments, such as but not limited to those described in paragraph [0130], the second duration of time is at least 2 minutes.

[0135] In some embodiments, such as but not limited to those described in paragraph [0130], the second duration of time is at least 15 minutes.

[0136] In some embodiments, such as but not limited to those described in paragraphs [0130]-[0135], wherein the second duration of time is not more than 60 minutes.

[0137] In some embodiments, such as but not limited to those described in paragraphs [0130]-[0135], the second duration of time is not more than 30 minutes.

[0138] In some embodiments, such as but not limited to those described in paragraphs [0130]-[0135], the second duration of time is not more than 20 minutes.

[0139] In some embodiments, such as but not limited to those described in paragraphs [0130]-[0134], the second duration of time is not more than 10 minutes.

[0140] In some embodiments, such as but not limited to those described in paragraphs [0130]-[0134], the second duration of time is not more than 5 minutes.

[0141] In some embodiments, such as but not limited to those described in paragraphs [0123]-[0140], the first temperature is at least the glass transition temperature of the polymer or at least 28° C., if the glass transition temperature is lower than 25° C., and not more than 60° C. above the glass transition temperature of the polymer, or not more than the melting temperature of the polymer, if the polymer exhibits a melting temperature, or not more than 78° C., whichever of the three that is above 28° C. is the lowest.

[0142] In some embodiments, such as but not limited to those described in paragraphs [0123]-[0140], the first temperature is at least the glass transition temperature of the polymer or at least 28° C., if the glass transition temperature is lower than 25° C., and not more than 100° C. above the glass transition temperature of the polymer, or not more than the melting temperature of the polymer, if the polymer exhibits a melting temperature, or not more than 120° C., whichever of the three above 28° C. is the lowest.

[0143] In some embodiments, such as but not limited to those described in paragraphs [0123]-[0140], the first temperature is at least the glass transition temperature of the polymer or at least 28° C., if the glass transition temperature is lower than 25° C., and not more than 15° C. above the glass transition temperature of the polymer, or not more than the melting temperature of the polymer, if the polymer exhibits a melting temperature, or not more than 43° C., whichever of the three above 28° C. is lowest.

[0144] In some embodiments, such as but not limited to those described in paragraphs [0123]-[0140], the first temperature is between 5° C. and 35° C. above the glass transition temperature of the polymer, or if the glass transition temperature is lower than 25° C., than at least 28° C. and not more than 43° C.

[0145] In some embodiments, such as but not limited to those described in paragraphs [0123]-[0140], the first temperature is between 5° C. and 35° C. above the glass transition temperature of the polymer, or if the glass transition temperature is lower than 25° C., than at least 30° C. and not more than 43° C.

[0146] In some embodiments, such as but not limited to those described in paragraphs [0123]-[0140], the first temperature is at least the glass transition temperature of the polymer or 28° C., if the glass transition temperature is lower than 25° C., and not more than 15° C. above the glass transition temperature of the polymer, or not more than the melting temperature of the polymer, if the polymer exhibits a melting temperature that is less than 15° C. above the glass transition temperature of the polymer, or not more than 43° C., if 15° C. above the glass transition temperature of the polymer is lower than 43° C.

[0147] In some embodiments, such as but not limited to those described in paragraphs [0123]-[0146], the higher temperature is the same temperature as or within 5° C. of the first temperature.

[0148] In some embodiments, such as but not limited to those described in paragraphs [0123]-[0146], the higher temperature is at least 5° C. above the first temperature, but not greater than 50° C. above the first temperature.

[0149] In some embodiments, such as but not limited to those described in paragraphs [0123]-[0146], the higher temperature is at least 10° C. above the first temperature, but not greater than 40° C. above the first temperature.

[0150] In some embodiments, such as but not limited to those described in paragraphs [0123]-[0146], the higher temperature is at least 15° C. above the first temperature, but not greater than 30° C. above the first temperature.

[0151] In some embodiments, such as but not limited to those described in paragraphs [0123]-[0146], if the polymer has a glass transition temperature that is lower than 25° C., the second temperature is in the range of 30° C. to 45° C.

[0152] In some embodiments, such as but not limited to those described in paragraphs [0123]-[0146], if the polymer has a melting that is greater than 25° C., the second temperature is at or above the melting temperature, but not greater than 100° C. above the melting temperature.

[0153] In some embodiments, such as but not limited to those described in paragraphs [0123]-[0146], if the polymer has a glass transition temperature that is greater than 25° C., the higher temperature is in the range of 25° C. and 75° C. above the glass transition temperature of the polymer.

[0154] In some embodiments, such as but not limited to those described in paragraphs [0123]-[0146], the higher temperature is not greater than the melting temperature, if there is a melting temperature that is at least 40° C., or not greater than the higher of not more than 50° C. above the glass transition temperature of the polymer, and 40° C.

[0155] In some embodiments, such as but not limited to those described in paragraphs [0105]-[0154], heating at least part of the polymer film to fuse the polymer film into a polymer tube is executed at a pressure ranging from 1 psi (50 Torr) to 250 psi (13,000 Torr).

[0156] A method of making a medical device body, the method including, but not limited to, grinding a polymer resin into a smaller particle size under cryogenic conditions; combining the ground particles with a lubricant which is a non-solvent for the polymer to form a slurry of the ground particles; forming the slurry into a partially consolidated device or a partially consolidated tube; and consolidating the tube or device.

[0157] In some embodiments, such as but not limited to that described in paragraph [0156], the cryogenic condition is a temperature of at least −150° C.

[0158] In some embodiments, such as but not limited to that described in paragraph [0156], the cryogenic condition is a temperature of at least −196° C. (±0.5° C.) or lower.

[0159] In some embodiments, such as but not limited to that described in paragraph [0156], the cryogenic condition is a temperature of at least −185.9° C. (±0.5° C.) or lower.

[0160] In some embodiments, such as but not limited to those described in paragraphs [0156]-[0159], the polymer is selected from the group consisting of poly(L-lactide), a copolymer where one constituent monomer is L-lactide, poly(glycolide), a copolymer where one constituent monomer is glycolide, poly(D,L-lactide), a copolymer where one constituent monomer is D,L-lactide, polydioxanone, poly(4-hydroxybutyrate), and poly(trimethylene carbonate), a copolymer where at least one constituent monomer is polydioxanone, poly(4-hydroxybutyrate), or poly(trimethylene carbonate), and combinations thereof; and the lubricant is selected from the group consisting of hydrocarbons or freons.

[0161] In some embodiments, such as but not limited to those described in paragraphs [0156]-[0160], the smaller particle size is an average particle size of about 0.1 to about 10 microns as measured by photon correlation spectroscopy, coulter counter, or light scattering.

[0162] In some embodiments, such as but not limited to those described in paragraphs [0156]-[0160], the smaller particle size is a number average particle size of about 0.01 to about 30 microns.

[0163] In some embodiments, such as but not limited to those described in paragraphs [0156]-[0160], the smaller particle size is a number average particle size of about 0.05 to about 25 microns.

[0164] In some embodiments, such as but not limited to those described in paragraphs [0156]-[0160], the smaller particle size is a number average particle size of about 0.1 to about 10 microns.

[0165] In some embodiments, such as but not limited to those described in paragraphs [0156]-[0164], the slurry comprises 20 weight % to 70 weight % polymer.

[0166] In some embodiments, such as but not limited to those described in paragraphs [0156]-[0165], forming the slurry into a partially consolidated device or a partially consolidated tube is performed with the polymer at a temperature not less than the glass transition temperature of the polymer, or not less than 28° C., whichever is higher, and not more than 15° C. above the glass transition temperature of the polymer, or not more than 43° C., whichever is higher.

[0167] In some embodiments, such as but not limited to those described in paragraphs [0156]-[0165], forming the slurry comprises extrusion.

[0168] In some embodiments, such as but not limited to those described in paragraph [0157], the extrusion is extrusion of a tube.

[0169] In some embodiments, such as but not limited to those described in paragraphs [0156]-[0165], forming the slurry comprises injection molding.

[0170] In some embodiments, such as but not limited to those described in paragraph [0169], the medical device is a stent formed by consolidation of injection molded polymer.

[0171] In some embodiments, such as but not limited to those described in paragraphs [0156]-[0169], the consolidation comprises sintering.

[0172] In some embodiments, such as but not limited to those described in paragraphs [0156]-[0171], the medical device is a stent formed from the consolidated tube.

BRIEF DESCRIPTION OF THE DRAWINGS

FIG. 1 depicts an exemplary stent.
FIGS. 2A-C depict a dip coating process.

DETAILED DESCRIPTION OF THE INVENTION

Figure 3:
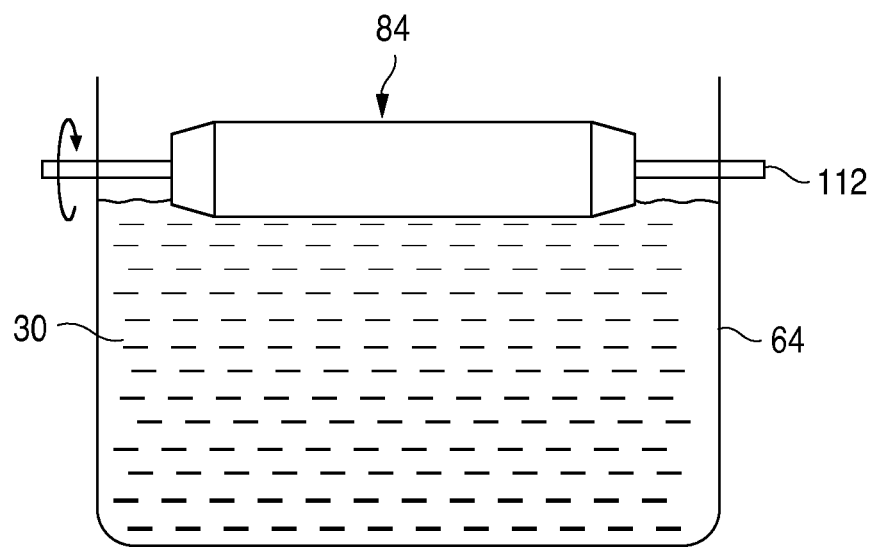
FIG. 3 depicts another dip coating process.

Use of the term "herein" encompasses the specification, the abstract, and the claims of the present application.

Use of the singular herein includes the plural and vice versa unless expressly stated to be otherwise. That is, "a" and "the" refer to one or more of whatever the word modifies. For example, "a drug" may refer to one drug, two drugs, etc. Likewise, "the stent" may refer to one, two or more stents, and "the polymer" may mean one polymer or a plurality of polymers. By the same token, words such as, without limitation, "stents" and "polymers" would refer to one stent or polymer as well as to a plurality of stents or polymers unless it is expressly stated that such is not intended.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the unmodified word or phrase. With the preceding discussion in mind, a numerical value herein that is modified by a word of approximation may vary from the stated value by ±15% in some embodiments, by ±10% in some embodiments, by ±5% in some embodiments, or in some embodiments, may be within the 95% confidence interval. As an example, the term "consisting essentially of" may be 85%-100% in some embodiments, may be 90%-100% in some embodiments, or may be 95%-100% in some embodiments.

As used herein, any ranges presented are inclusive of the end-points. For example, "a temperature between 10° C. and 30° C." or "a temperature from 10° C. to 30° C." includes 10° C. and 30° C., as well as any temperature in between. In addition, throughout this disclosure, various aspects of this invention may be presented in a range format. The description in range format is merely for convenience and brevity and should not be construed as an inflexible limitation on the scope of the invention. Accordingly, the description of a range should be considered to have specifically disclosed all the possible subranges as well as individual numerical values, both integers and fractions, within that range. As an example, a description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. Unless expressly indicated, or from the context clearly limited to integers, a description of a range such as from 1 to 6 should be considered to have specifically disclosed subranges 1.5 to 5.5, etc., and individual values such as 3.25, etc. This applies regardless of the breadth of the range.

A stent or scaffold is a type of medical device, specifically an implantable medical device. As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants, prostheses, vascular grafts, self-expandable stents, stent-expandable stents, stent-grafts, grafts, artificial heart valves, foramen ovale closure devices, cerebrospinal fluid shunts, orthopedic fixation devices, and intrauterine devices.

Other medical devices may be referred to as insertable medical devices that are any type of appliance that is totally or partly introduced, surgically or medically, into a patient's body or by medical intervention into a natural orifice, but the device does not remain in the patient's body after the procedure.

As noted above, a stent is a type of implantable medical device. Stents are generally cylindrically shaped and function to hold open, and sometimes expand, a segment of a blood vessel or other vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease. A stent can be used in, without limitation, the cerebral, neuro, carotid, coronary, pulmonary, aortic renal, biliary, iliac, femoral (superficial femoral artery) and popliteal vasculature, as well as other peripheral vasculatures, and in other bodily lumens such as the urethra, bile duct, or tear duct. A stent can be used in the treatment or prevention of disorders such as, without limitation, atherosclerosis, vulnerable plaque, thrombosis, restenosis, hemorrhage, vascular dissection and perforation, vascular aneurysm, chronic total occlusion, claudication, anastomotic proliferation, bile duct obstruction and ureter obstruction.

Another type of medical device is a vascular catheter, which is a type of insertable device. A vascular catheter is a thin, flexible tube with a manipulating means at one end, referred to as the proximal end, which remains outside the patient's body, and an operative device at or near the other end, called the distal end, which is inserted into the patient's artery or vein. The catheter may be introduced into a patient's vasculature at a point remote from the target site, e.g., into the femoral artery of the leg where the target is in the vicinity of the heart. The catheter is steered, assisted by a guide wire than extends through a lumen, which is a passageway or cavity, in the flexible tube, to the target site whereupon the guide wire is withdrawn. After the guidewire is withdrawn, the lumen may be used for the introduction of fluids, often containing drugs, to the target site. For some vascular catheters there are multiple lumens allowing for the passage of fluids without removal of the guidewire. A catheter may also be used to deliver a stent or may be used to deliver a balloon used in angioplasty.

As used herein, a "balloon" refers to the well-known in the art device, usually associated with a vascular catheter, that comprises a relatively thin, flexible material, forming a tubular membrane, that when positioned at a particular location in a patient's vessel may be expanded or inflated to an outside diameter that is essentially the same as the inside or luminal diameter of the vessel in which it is placed. In angioplasty procedures, the balloon is expanded to a size larger than the luminal diameter of the vessel, as it is a diseased state, and closer to the luminal size of a healthy reference section of the vessel. In addition to diameter, a balloon has other dimensions suitable for the vessel in which it is to be expanded. Balloons may be inflated, without limitation, using a liquid medium such as water, aqueous contrast solution, or normal saline solution, that is, saline that is essentially isotonic with blood.

A "balloon catheter" refers to medical device which is a system of a catheter with a balloon at the end of the catheter.

A balloon, a catheter, and a stent differ. Stents are typically delivered to a treatment site by being compressed or crimped onto a catheter or onto a catheter balloon, and then delivered through narrow vessels to a treatment site where the stent is deployed. Deployment involves expanding the stent to a larger diameter, typically to the diameter of the vessel (or closer to the luminal size of a healthy reference section of the vessel), once it is at the treatment site. Stents can be self-expanding or balloon expandable. The expanded stent is capable of supporting a bodily lumen for an extended period of time. In contrast, a balloon has a wall thickness that is so thin that the tubular membrane cannot support a load at a given diameter unless inflated with a fluid, such as a liquid or gas. Furthermore, a balloon is a transitory device that is inserted in the patient's body for only a limited time for the purpose of performing a specific procedure or function. Unlike a stent, dilatation balloons are not permanently implanted within the body. Moreover, vascular catheters have a length to diameter ratio of at least 50/1.

The structure of a stent is typically a generally cylindrical or tubular form (but the precise shape may vary from the shape of a perfect cylinder), and the tube or hollow cylinder may be perforated with passages that are slots, ovoid, circular, similar shapes, or any combination thereof. The perforations extend over the length of the stent, rather than being concentrated in one region of the stent. In some embodiments, the perforations form at least 10%, preferably at least 20%, more preferably at least 25%, and even more preferably at least 30%, but not more than 99% of the exterior surface area of the tube. A stent may be composed of scaffolding that includes a pattern or network of interconnecting structural elements or struts. The scaffolding can be formed from tubes, or sheets of material, which may be perforated or unperforated, rolled into a cylindrical shape and welded or otherwise joined together to form a tube. A pattern may be formed in the tube by laser cutting, chemical etching, etc.

An example of a stent 100 is depicted in FIG. 1. As noted above, a stent may be a scaffolding having a pattern or network of interconnecting structural elements or struts 105, which are designed to contact the walls of a vessel and to maintain vascular patency, that is to support the bodily lumen. Struts 105 of stent 100 include luminal faces or surfaces 110 (facing the lumen), abluminal faces or surfaces 115 (tissue facing), and sidewall faces or surfaces 120. The pattern of structural elements 105 can take on a variety of patterns, and the structural pattern of the device can be of virtually any design. Typical expanded diameters of a stent range from approximately 1.5 mm to 35 mm, preferably from approximately 2 mm to 10 mm, and for a coronary stent, from 1.5-6.0 mm. The length to diameter ratio of a stent is typically from 2 to 25. The embodiments disclosed herein are not limited to stents, or to the stent pattern, illustrated in FIG. 1.

Other types of endoprotheses or stents are those formed of wires, such as the Wallsten endoprosthesis, U.S. Pat. No. 4,655,771, and those described in U.S. Pat. No. 7,018,401 B1 and U.S. Pat. No. 8,414,635 B2. Those described in U.S. Pat. No. 7,018,401 B1 and U.S. Pat. No. 8,414,635 B include, but are not limited to, a plurality of shape memory wires woven together to form a body suitable for implantation into an anatomical structure. These devices may be of a substantially uniform diameter, or may have a variable diameter such as an hourglass shape. Other stent forms include helical coils.

The body, scaffolding, or substrate of a stent may be primarily responsible for providing mechanical support to walls of a bodily lumen once the stent is deployed therein. The "device body" of a medical device may be the functional device without a coating or layer of material different from that of which the device body is manufactured has been applied. If a device is a multi-layer structure, the device body may be the layer(s) that form the functional device, and for a stent this would be the layer(s) which support the bodily lumen. For a stent, the stent body may be the scaffolding, for example, as pictured in FIG. 1, without an exterior coating. If the body is manufactured by a coating process (typically many layers), the stent body can refer to a state prior to application of additional coating layers of different material. "Outer surface" of an implantable device, such as a stent, refers to any surface however spatially oriented that is in contact, or may be in contact, with bodily tissue or fluids. As a non-limiting example, for the stent shown in FIG. 1, the outer surface includes the abluminal surface, the luminal surface, and the sidewall surfaces.

Implantable and insertable medical devices can be made of virtually any material including metals and/or polymers including both polymers, biostable polymers, and combinations thereof.

Although stents made of nonerodible metals and metal alloys have become the standard of care for treatment of artery disease, it is desirable to make stents out of polymers, and especially biodegradable polymers. Obviously, a stent or other device formed of a biostable or durable material would remain in the body until removed. There are certain disadvantages to the presence of a permanent implant in a vessel such as compliance mismatch between the stent and vessel and risk of embolic events. The presence of a stent may affect healing of a diseased blood vessel. To alleviate such disadvantages, stent can be made from materials that erode or disintegrate through exposure to conditions within the body. Thus, erodible portions of the stent can disappear from the implant region after the treatment is completed, leaving a healed vessel. Stents fabricated from biodegradable, bioabsorbable, and/or bioerodable materials such as polymers can be designed to completely erode only after the clinical need for them has ended.

Embodiments of the present invention encompass, but are not limited to, devices that are bioabsorbable. As used herein, the terms "biodegradable," "bioabsorbable," "bioresorbable," and "bioerodable" are used interchangeably and refer to materials, such as but not limited to, polymers, which are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes. Conversely, the term "biostable" refers to materials that are not biodegradable, or biodegrade over a very long time period, such as over two or more decades.

The stent must be able to satisfy several mechanical requirements. The stent must have radial strength and sufficient strength and rigidity to support the walls of a vessel and withstand radially compressive forces. Longitudinal flexibility is required for delivery and deployment. Relatively high toughness or resistance to fracture is required for the material of the stent must be able to withstand crimping onto a delivery element, such as the balloon of a vascular catheter, as well as expansion when deployed. It must maintain its shape once deployed. For stents used in the superficial femoral artery (SFA), the mechanical requirements can be higher than for stents in coronary arteries as the SFA is subjected to various forces, such as compression, torsion, flexion, extension, and contraction, which place a high demand on the mechanical performance of implants. The mechanical requirements on a stent differ from those of other implantable medical devices such as catheters, which are not crimped to a smaller size and/or expanded.

Although biodegradable polymers can de designed to erode away, one drawback of polymers as compared to metals and metal alloys is that the strength to weight ratio of polymers is usually smaller than that of metals. To compensate for this, a polymeric stent can require significantly thicker struts than a metallic stent, which results in an undesirably large profile. For example, a typical thickness for a strut in a metal stent is about 0.003".

To avoid large struts, polymers may be processed to improve strength and toughness. The use of polymers of higher molecular weights may also contribute to strength and toughness of the stent. The use of high molecular weight polymers may be used instead of, or in addition to, processing operations to increase polymer strength.

An example of some of the process operations that may be involved in fabricating a polymeric stent include, but are not limited to, the following:

(1) forming a polymeric tube using extrusion or injection molding, or by rolling and welding a polymer sheet which may be formed by extrusion, injection molding, solvent casting or another process;

(2) radially deforming, axially deforming, or both (expanding, extending, or both expanding and extending) the formed tube by application of heat and/or pressure;

(3) forming a stent from the deformed tube by cutting a stent pattern in the deformed tube such as with chemical etching or laser cutting;

(4) optionally coating the stent with a coating including a drug;

(5) crimping the stent on a support element, such as a balloon on a delivery catheter;

(6) packaging the crimped stent/catheter assembly; and (7) sterilizing the stent assembly.

A noted in step (2), an extruded polymer tube may also be radially expanded, axially extended, or both radially expanded and axially extended to increase its radial strength, which can also increase the radial strength of the stent. The radial expansion process tends to preferentially align the polymer chains along the radial or hoop direction which is believed result in enhanced radial strength. The tube at both the initial and expanded diameter have wall thicknesses that are large enough that they can support an inward radial force or load. The radial expansion and axial extension may occur sequentially with either the radial expansion and the axial extension occurring first in time, and there may be a 15 second to 3 hour delay between the two operations. The radial expansion and axial extension may occur concurrently, where at least 50% of time, at least 70% of the time, or at least 90% of the time that the tube is being expanded, the tube is also being extended, or vice versa.

During the expansion step, the tube is heated to a temperature between glass transition temperature ($T_g$) (if the polymer has a glass transition temperature greater than about 25° C.), and the melting point of the polymer, if the polymer exhibits a melting point, and the tube is expanded to an expanded diameter. Upon expansion the tube is cooled to below the Tg of the polymer, typically to ambient temperature (20° C. to 30° C.), to maintain the tube at an expanded diameter. The percent radial expansion may be between about 50% and 600%, preferably 300% to 500%, or any specific value within either of these ranges, such as about 400%. The percent radial expansion is defined as RE %=(RE ratio−1)×100%, where the RE Ratio=(Inside Diameter of Expanded Tube)/(Original Inside Diameter of the Tube). The percent axial extension expansion may be between about 10% and about 200%, preferably between about 15% and about 120%, or any specific value within either of these ranges, such as about 20%. The percent of axial extension that the polymer tube undergoes is defined as AE %=(AE ratio−1)×100%, where the AE Ratio=(Length of Extended Tube)/(Original Length of the Tube). The expansion of the tube decreases the wall thickness from about 300 to 600 microns (microns=micrometers, $10^{-6}$ meters) to a thickness in the range about 70 to about 200 microns. The width and thickness of the struts of the stent can be, for example, between 90-160 microns.

After cutting a stent pattern into the expanded tube, as noted in step (4) the stent scaffolding may then be optionally coated with a coating which can include a polymer and a drug. The drugs may be distributed uniformly or non-uniformly in a coating that is disposed over all of, substantially all of, or at least a portion of, the outer surface of the device.

In order to make the stent ready for delivery, the stent is secured to a delivery element such as a delivery balloon. In this process, the stent is compressed to a reduced diameter or crimped over the balloon. During crimping and in the crimped state, some sections of the stent are subjected to high, localized stress and strain. Due to the fact that some regions of the stent structure are subjected to high compressive stress and strain, the stent during crimping and in the crimped state may be susceptible to cracking.

The stent is deployed by expanding it to an increased diameter at an implant site in a vessel which can be greater than the as-cut diameter of the stent. The deployed stent must have sufficient radial strength to apply an outward radial force to support the vessel at an increased diameter for a period of time.

Some of the methods used to form a stent or methods of forming a polymer tube or a polymer construct from which a stent is formed involve processing at high temperatures, such as at and/or above the melting point of the polymer. In addition, methods such as extrusion subject the polymer to high shear stresses. The exposure to high shear, to high temperatures, or both, may result in degradation of the polymer. The degradation may reduce the molecular weight of the polymer, and thus, potentially reduce the strength of the polymer. For higher molecular weight polymers, higher temperatures are needed to obtain a viscosity sufficiently low for processing, which may lead to even more degradation which may reduce the molecular weight.

As used herein, "polymer construct" refers to any useful article of manufacture made of a polymer. A polymer construct may be further processed to form a medical device. Some examples of polymer constructs include, but are not limited to, a tube, a sheet, a fiber, etc.

Various embodiments of the present invention encompass methods of forming a medical device, such as a stent, having a device body or scaffolding formed or fabricated from a polymer. The various embodiments of the present invention encompass methods of solvent or other processing of the polymer such that the polymer is processed at a lower temperature, and with lower exposure to shear stress.

Although the discussion that follows may make reference to a stent or stents as the medical device, the embodiments of the present invention are not so limited, and encompass any medical device which may benefit from the embodiments of the invention. Examples of the other types of medical devices which may benefit from the embodiments of the present invention, include, without limitation, extravascular wraps, intrapulmonary or intra-urethral stents, stents for other than vascular lumens, drug delivery devices including implantable drug delivery devices, and any substrate that may be used to support a surgical procedure, such as and without limitation, a device used to support an anastomotic site via minimally invasive bypass surgery. As used herein, "polymeric stent" refers to a stent having a scaffolding (or body) that is made completely, or substantially completely, from a polymer, or the scaffolding is made from a composition including a polymer and a material. If the scaffolding is made from a composition including a polymer and a material, the polymer is a continuous phase of the scaffolding, the scaffolding is at least 50% by weight polymer, or the scaffolding is at least 50% by volume polymer. In some embodiments, a polymeric stent may have a scaffolding made from a composition including a polymer and a material that is at least 70%, at least 80%, at least 90%, or at least 95% by volume or by weight polymer, but not more than 99.5% by volume or by weight. Analogous definitions apply to a polymeric tube, a polymer construct, or a polymeric medical device except that the reference to the scaffolding would be replaced by "tube" for a polymer tube, "construct" for a polymer construct, and "device body" for a medical device. In some embodiments, the polymeric scaffolding, polymeric construct, polymer tube, or polymeric device, is free of drugs, or essentially free of drugs (not more than 0.01 weight %, or not more than 0.001 weight % drug).

Some processes, such as melt extrusion and radiation sterilization, result in a decrease in the molecular weight of the polymer. Thus, in some embodiments, the formation of a polymer construct, such as a tube, from which the device, such as a stent, is formed using solvent processing methods. Solvent processing generally refers to forming a polymer construct such as a tube from a mixture of a polymer and a solvent. Non-limiting examples of solvent processing methods include spray coating, gel extrusion, supercritical fluid extrusion, roll coating and dip coating. In some embodiments, the polymer construct, such as a tube, is formed by ram extrusion, compression molding, or both, which may result in less polymer degradation than traditional melt processing operations.

Solvent processing methods include the use of gel extrusion, as described in patent application Ser. No. 11/345,073 (United States Patent Application Publication No. 2007-0179219 A1, published on Aug. 2, 2007), which is incorporated by reference herein in its entirety.

Another preferred solvent processing method is dip coating. Dip coating is a method of forming a material layer on an object which includes immersing the object in a solution of a material, which is this case is a polymer, where the polymer (and optionally another material) may be dissolved, partially dissolved, dispersed, or a combination thereof, in a solvent, withdrawing the object from the solution, and removing solvent from the solution retained on the surface of the object. In preferred embodiments, the polymer is dissolved in the solvent. As used herein, with reference to a polymer solution for forming a polymer construct by dipping, spraying, or gel extrusion, a "solvent" is defined as a substance that dissolves one or more substances, partially dissolving the substance(s), disperses the substance(s), or a combination thereof, to form a uniformly dispersed solution at a selected temperature and pressure. A solvent can refer to one chemical compound, or a mixture of chemical compounds. A solvent can be a fluid. Upon removal of the solvent, a layer of polymer is formed on the surface of the object. The steps above can be repeated to form multiple layers of polymer (optionally including another material) over the object to obtain a desired thickness of a polymer tube on the object.

The object can be a cylindrical member or mandrel over which a polymer tube is formed. The mandrel can be made of any material that is not soluble in the solvent of the polymer solution. In some embodiments, the mandrel is made of a metal such as aluminum or stainless steel. In other embodiments, the mandrel is made from a glass with a polished surface. In some other embodiments, the mandrel is made of a soluble material that is insoluble in the solvent used for the coating. In other embodiments, the mandrel is made of a polymer. The polymer tube may be formed so that its radial thickness or the thickness of the wall of the polymer tube is the desired thickness of a stent scaffolding. The polymer tube may then be removed from the mandrel and machined to form a stent scaffolding.

FIGS. 2A-C illustrate a dipping or dip coating process. As shown in FIG. 2A, a mandrel 202 is lowered, as shown by an arrow 206 into a container 204 having a polymer solution 200 that includes a polymer, and optionally including an additive dissolved, dispersed, or both dissolved and dispersed in the solution. As shown in FIG. 2B, at least part of the mandrel remains immersed in solution 200 for a selected time or dwell time. In some embodiments, the mandrel is only partially immersed in the solution. Referring to FIG. 2C, mandrel 202 is then removed from solution 200 as shown by an arrow 212. Solution 210 is retained on mandrel 202 after removal from the solution 200 in container 204. Solvent is then removed from the retained solution 210 which results in the formation of a tubular layer of the polymer, and optionally any additives or other materials also included in the solution. The dipping and drying is optionally repeated one or many times.

Between dips, the solvent can be removed using various types of drying methods. The solvent can be removed from the solution retained on the mandrel by methods known in the art including air drying, baking in an oven, or both. As used herein, "removing the solvent" or "solvent is removed" includes allowing the solvent to evaporate, as well as use of other means to increase the rate of solvent evaporation. In air drying a gas stream is directed on or blown onto the mandrel. The gas can be at room temperature (about 20° C. to about 25° C.) or heated (a temperature in the range of about 30° C. to about 90° C.) to increase the removal rate. In some embodiments, drying is done at reduced pressure such as less than 200 Torr, or less than 100 Torr, but at least 0.001 Torr.

For the method described above, as shown in FIG. 2A, the cylindrical axis of the mandrel is perpendicular to the surface of the solution, although the mandrel can be immersed at an angle different from 90° to the solution surface. Similarly, as shown in FIG. 2C, the cylindrical axis of mandrel 202 is perpendicular to the surface of the solution when removed, although the mandrel can be removed at angle different from 90° to the solution surface. The use of a 90° angle is expected to facilitate uniformity in the polymer tube thickness. In some embodiments, the mandrel is dipped, removed, or both, horizontally, that is at an angle that is parallel to the surface of the solution (0°), with a variation of up to ±5°, ±10°, or ±15° from perfectly parallel. In some embodiments, the mandrel is dipped, removed, or both, at an angle that is between parallel (0°) and perpendicular (90°), such as, without limitation, between 20° and 70°, or about 45°. In some embodiments, the cylindrical axis of the mandrel is parallel with the surface of the solution upon immersion and removal, and between dips the mandrel is rotated at least 360° about its cylindrical axis, but not more than 100 complete rotations (1 complete rotation is 360°).

Other dipping processes can be envisioned by those skilled in the art. These include immersing only a small part of the mandrel into the solution and while rotating parallel to the solution. This process helps ensure an even polymer tube thickness. A non-limiting example is shown in FIG. 3 where a mandrel 84 is attached to a support assembly 112, positioned so that only the part of the outer surface of the mandrel 84 is in contact with, or partially immersed in the surface of the polymer solution 30 as disposed in reservoir 64. The support assembly 112 rotates the mandrel 84 such that only part of the surface is in contact or immersed in the polymer solution. As shown in FIG. 3, the mandrel is parallel to the surface of the solution, and may vary by ±5°, ±10°, or ±15° from perfectly parallel. The cylinder while partially immersed may be rotated only part of a rotation (at least 5° but not more than 360°), such as between 5° and 275°, between 5° and 180°, or between 180° and 360°. In some embodiments, the mandrel is rotated more than one complete rotation, such as between 360° to 720°, or in some embodiments, more than 2 complete rotations, but not to exceed 1000 complete rotations. In some embodiments, the mandrel may be periodically removed from the solution entirely (raised), and rotated one or more times (at least one complete rotation, not to exceed 1000) to remove at least a portion of the solvent. The mandrel may be then again be positioned such that only part of the surface is in contact with or immersed in the polymer solution, and following the positioning, rotation of the mandrel, and subsequently followed by removal and rotation, etc. The immersion into the solution and rotation followed by removal with optional rotation as described above may be repeated on one or more occasions (in some embodiments, the sequence of removal and rotation followed by removal from the solution and rotation is repeated at least twice).

In another embodiment, a hollow mandrel is dipped into the solution of the polymer, optionally including an additive, and a vacuum is drawn at one end of the mandrel causing the solution to be drawn into the mandrel. When the mandrel is lifted from the solution, the solution will drain from the inside leaving the inside to the mandrel coated with the polymer forming a polymer tube.

There are several parameters in the dipping process that can affect the quality and uniformity of the polymer tube, typically built of multiple layers of polymer. It is desirable for the polymer tube to be uniform circumferentially and along the cylindrical axis. Parameters include the concentration and viscosity of the polymer solution, the dwell time in solution, and the rate of removal of the mandrel from solution.

In some embodiments, polymer concentration can be at or near (within 10%) a saturation concentration. Such concentration is expected to result in the highest viscosity and the thickest polymer layer per immersion. In some embodiments, the polymer concentration may be limited to a viscosity of not more than 10,000 centiPoise (cP), and preferably, not more than 7,500 cP, but at a viscosity of at least the pure solvent. Alternatively, polymer concentration can be less than saturation, for example, less than 50% or less than 25% saturation. A more dilute and less viscous solution may result in a more uniform polymer layer. However, a more dilute solution will require a higher number of repeated dipping steps to provide a final desired polymer tube thickness.

The dip coating process allows for use of a different solution for one or more dips allowing some solutions to include drugs, radiopaque agents, or other additives, in addition to or instead of the polymer. Thus, there may be concentration gradients of an additive, such as a drug, across the thickness of the tube, and the device formed from such a polymer tube.

There are various ways to remove the polymer tube from the mandrel to further process the polymer tube in the fabrication of a stent. Methods include using a dissolvable material as a coating on the mandrel, and dissolving it after the tube is the proper thickness. As a non-limiting example, the mandrel is a wax and the coating polymer is PLLA. If a hollow mandrel is used and the polymer forms a seal over one end, then compressed air blow into the other open end forces the tube off the mandrel. In some embodiments, the "mandrel" is an inflated tubular balloon which is deflated after the dip coating and solvent removal is complete (or solvent removal is complete to about 10 weight % or less). Other methods include the use of a solvent to swell the polymer or a greasy or oily coating on the mandrel either of which allows the polymer tube to be slipped off the mandrel. Heating or cooling of the polymer tube, the mandrel, or both may be used to assist in the removal of the tube. In some embodiments, a mandrel made of poly(tetrafluoroethylene), poly(tetrafluoroethylene-co-hexafluoropropylene), Kel-F® poly(chlorotrifluoroethylene), poly(vinylidene fluoride), poly(vinylidene fluoride-co-chlorotrifluoroethylene, or other fluoropolymer is used.

In some embodiments, instead of, or in addition to, dipping, the polymer solution may be sprayed onto a mandrel. Spray coating is another solvent processing method which may be used to form a tube or other construct, and is described in United States Patent Application Publication No. 2010-0262224 A1, published on Oct. 14, 2010, which is incorporated by reference herein in its entirety.

Embodiments of the spraying method may include an operation including spraying the polymer solution over the mandrel, and then drying the mandrel to substantially remove the solvent (at least 80 weight %, at least 90 weight %, at least 95 weight %, or at least 98 weight % of the solvent in the solution is removed during the spraying process, drying between spraying process, or both processes). The procedure of spraying and drying may be optionally repeated one or more time until a desired thickness of polymer has been deposited onto the mandrel. In preferred embodiments, the polymer solution is atomized through pressure or ultrasound, and the spraying operation may use an external gas assisted atomizer, an internal gas assisted atomizer, a nebulizer, a rotating disc sprayer, or an ultrasonic sprayer. During the spraying process, relative to the sprayer or applicator, the mandrel may be rotated, translated, or both.

Dipping and spraying operations may both be used to form a polymer tube or a polymer construct. As a non-limiting example, several tubular polymer layers may be applied to a mandrel or other cylindrical member by dipping, followed by application of more tubular polymer layers by spraying, and optionally following by dipping and spraying on one or more occasions to form one or more additional tubular polymer layers.

In preferred embodiments, a polymer tube is formed of poly(L-lactide) or a polymer in which at least one constituent monomer is L-lactide, preferably at least 50 mol % L-lactide, by a solvent processing operation, the operation being a dipping operation, a spraying operation, or a combination thereof. The solvent for the polymer solution for the solvent processing operation may be methylene chloride, chloroform, acetone, 2-butanone, cyclohexanone, tetrahydrofuran, dioxane, 1,1,1, trichloroethane, trichloroethylene, and combinations thereof.

Another method of forming a tubular medical device, such as a stent, is to roll a sheet in to the shape of a tube and join the edges together such as by, without limitation, welding, heat sealing, use of an adhesive, or a combination thereof. Roll coating of a web or other means of solvent casting followed by drying to form a film is well known in the art. In some embodiments of the present invention, the web may act as a release layer, allowing the film to be separated from the web. The web should be reasonably stiff to prevent stretching of the web during application of a polymer solution (in which the polymer, and optionally another material, may be dissolved, partially dissolved, dispersed, or a combination thereof in the solvent). As used herein, with reference to a solvent used in a polymer solution for a web coating operation, a "solvent" is defined as a substance that dissolves one or more substances, partially dissolving the substance(s), disperses the substance(s), or a combination thereof, to form a uniformly dispersed solution at a selected temperature and pressure. A solvent can refer to one chemical compound, or a mixture of chemical compounds. A solvent can be a fluid. With respect to web coating, the solvent can be removed from the solution retained on the web by methods known in the art including air drying, baking in an oven, or both. In air drying a gas stream is directed on or blown onto the web. The gas can be at room temperature (about 20° C. to about 25° C.) or heated (a temperature in the range of about 30° C. to about 90° C.) to increase the removal rate. In some embodiments, drying is done at reduced pressure such as less than 200 Torr, or less than 100 Torr, but at least 0.001 Torr.

In some embodiments, solvent may be removed to a level such as less than 2 weight %, less than 1 weight %, less than 0.5 weight %, less than 0.2%, or less than 0.1 weight % solvent in the polymer film before the film is removed from the web. In other embodiments, solvent may be removed to a level such as 2 weight % to 12 weight % solvent in the polymer film before the film is removed from the web.

In a production line, the solution would be cast or rolled onto a web or substrate which is on rollers and may subsequently move through an oven or a heated section.

As the polymer film is separated from the web it may be wrapped around a cylindrical member such as a mandrel, or roller. In some embodiments, the film edges just touch each other, and in other embodiments, there is some overlap where one edge of the film at least partially covers the other edge of the film already wrapped around the mandrel. In some embodiments, the overlap is not more than 2%, not more than 5%, or not more than 10% of the surface area of the film, but at least 0.005%. In some embodiments, more than 30% of the surface area overlaps. In some embodiments, the polymer film is wrapped around the cylindrical member at least 1 complete time, but less than 2 complete times. In some embodiments, the polymer film is wrapped around the cylindrical member at least 2 times, at least 5 times, at least 7 times, or at least 10 times, but not more than 100 times. In some embodiments, the polymer film is wrapped around the cylindrical member not more than 4 complete times, or the polymer tube thickness is not more than 4 times the thickness of the polymer film. The number of times that the film is wrapped entirely around the mandrel depends upon the thickness of the film, and the desired thickness of the final tube. The final formed polymer tube may be of the same thickness of the final device, or may be thicker if the tube will be subject to further processing that may reduce the wall thickness, such as, and without limitation, radial expansion.

In some embodiments, the wrapping may be executed at room temperature (about 20° C. to about 25° C.), or when the polymer is at its glass transition temperature (±3° C.), or at a temperature that is not less than the glass transition temperature of the polymer (or at least 28° C., if the glass transition temperature is lower than 25° C.), and not more than the melting temperature of the polymer, if the polymer has a melting temperature, or if the polymer does not have melting temperature, not more than 50° C. above the glass transition temperature of the polymer or not more 40° C., whichever of the three is higher. If the polymer exhibits more than one glass transition temperature, then the heating may be above the highest, above the lowest, or above the or an intermediate glass transition temperature (if one or more exist), and one of skill in the art will be able to determine the appropriate glass transition temperature if more than one exists based on the objective of having the polymer film be sufficiently pliable to wrap around the cylindrical member or mandrel. In some embodiments, the wrapping occurs when the polymer film is at a temperature not less than the glass transition temperature of the polymer, and not more than 15° C. above the glass transition temperature of the polymer, or if the polymer exhibits a melting temperature and the melting temperature of the polymer is less than 15° C. above the glass transition temperature of the polymer, the melting temperature of the polymer. Typically, the polymer film may be heated to the target temperature prior to the beginning of the wrapping operation, and may be maintained at the temperature for at least the duration of the wrapping operation.

The tube may be formed from the wrapped polymer film by joining or sealing the edges if only the edges touch. The edges may be sealed by heating the edges and pressing the edges together to form a seal. The heating may be above the glass transition temperature of the polymer, such as between 5° C. and 35° C. above the glass transition temperature, or if the glass transition temperature is lower than 25° C., than at least 28° C., and preferably at least 30° C., and not more than the melting temperature of the polymer, if the polymer has a melting temperature, or if the polymer does not have melting temperature, not more than 60° C. or not more than 100° C. above the glass transition temperature of the polymer, whichever is higher. If the polymer exhibits more than one glass transition temperature, then the heating may be above the highest, above the lowest, or above an intermediate glass transition temperature. One of skill in the art will be able to determine the appropriate glass transition temperature if more than one exists based on the objective sealing the edges together to form a polymer tube. If the polymer also exhibits one or more melting temperatures, the heating may be above the or any of the melting temperatures of the polymer, and one of skill in the art can select the appropriate melting temperature if more than one exists. In some embodiments, only the polymer at or near the edges is heated. In other words, the entire polymer film may not be heated to a higher temperature. However, in some embodiments, the entire polymer film is heated.

Alternatively or additionally, an adhesive may be placed at one or both of the edges. In some embodiments, a solvent may be added to the edges to swell the polymer along the edge with the result being a "solvent" weld resulting from some of the polymer chains at the edges becoming entangled with polymer chains from the other edge. The use of the solvent may be combined with heating of the polymer, the use of an adhesive, or both.

Similar methods may be used if the polymer film overlaps except that the seal may be over the entire overlap region. If multiple layers are wrapped around the mandrel, the polymer film may be fused or sealed by heating the polymer, and optionally applying pressure to the polymer. The temperature to which the polymer is heated may be between the glass transition temperature of the polymer (or at least 28° C. if the glass transition temperature is lower than 25° C., preferably at least 30° C., and in some embodiments, at least 32° C.), and the melting temperature, if the polymer exhibits a melting temperature of at least 60° C., or if the polymer does not exhibit a melting temperature, a temperature that is not more than 60° C., or not more than 100° C. above the glass transition temperature, whichever is higher. In some embodiments, if the polymer has a melting temperature, the fusing is executed by heating the polymer to at, or above, such as within 25° C. of, the melting temperature. Similar to the situation with the wrapping, if the polymer exhibits more than one glass transition temperature, then the heating may be above the highest, above the lowest, or above an intermediate glass transition temperature, and one of skill in the art will be able to determine the appropriate glass transition temperature if more than one exists based on the objective of the objective of fusing the polymer film to form a tube. Similarly, if the polymer has more than one melting point, the upper limit of the temperature range for fusing the polymer film may be the lowest, the highest, or an intermediate melting point.

In some embodiments, the temperature to which the polymer film is heated to fuse the polymer film into a tube may be the same temperature as or within 5° C. of the temperature of the wrapping operation. In some embodiments, the temperature for fusing the film together to form a tube may be above, such as at least 5° C. above but not more than 50° C. above, the temperature of the polymer film during the wrapping operation. As a non-limiting example, for a polymer with a glass transition temperature not lower than 25° C., the wrapping may be executed with the polymer at a temperature between the glass transition temperature, and 15° C. above the glass transition temperature, and the subsequent fusing executed after the polymer film is heated to (and maintained at) a higher temperature, but not in excess of the melting temperature, or if the polymer does not have a melting temperature, not more than 50° C., such as a temperature between 25° C. and 45° C. above the glass transition temperature. For those polymers that have a glass transition temperature is lower than 25° C., the wrapping may be done at room temperature, and the fusing at a temperature in the range of 30° C. to 45° C., or at or above the melting temperature, if the polymer has a melting temperature that is greater than 25° C.

In some embodiments, the wrapping may be executed with the polymer at a temperature between 5° C. and 15° C. above the glass transition temperature (for a polymer with a transition temperature is equal to or greater than 25° C.), and the subsequent fusing executed after the polymer film is heated to (and maintained at) a higher temperature, such as between 25° C. and 75° C. above the glass transition temperature. In some embodiments, the temperature for fusing the film together to form a tube may be at least 10° C. above, but not greater than 40° C. above, or at least 15° C. above, but not greater than 30° C. above, the temperature of the polymer film during the wrapping operation.

In some embodiments, the tube is maintained at the temperature of the wrapping operation after the wrapping is complete for a duration of time ranging from at least 10 seconds, at least 10 seconds, at least 30 seconds, at least 60 seconds, at least 2 minutes, or at least 5 minutes, and not more than 120 minutes, then the polymer film is heated to a higher temperature for the fusing operation. In some embodiments, the tube is maintained at the temperature of the wrapping operation after the wrapping is complete for not more than 30 minutes. After the polymer is heated to the higher temperature for the fusing operation, the polymer may be maintained at the higher temperature for a duration ranging from at least 5 seconds, at least 30 seconds, at least 60 seconds, or at least 2 minutes, but not more than 5 minutes, not more than 10 minutes, not more than 20 minutes, or not more 60 minutes. In some embodiments, the duration of the fusing operation is between 15 minutes and 30 minutes.

The fusing operation may be carried out under pressure. The pressure may range from 1 psi (50 Torr) to 250 psi (13,000 Torr).

Figure 4:
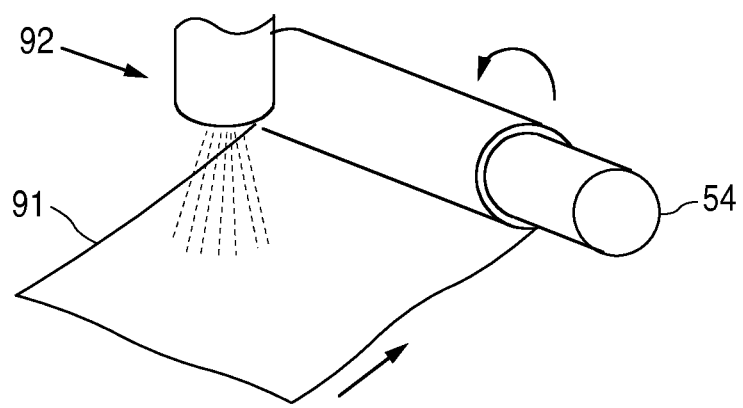
FIG. 4 depicts a method of forming a polymer tube.

In some embodiments, an adhesive, a solvent, or both, may be used in conjunction with heat, pressure, or both. A thin layer of an adhesive may be applied to one side of the film before or after the film is removed from the web. A solvent which at least partially swells the polymer (at least 1 weight % absorption of solvent) may be applied to one side of the film before, or during the wrapping of the film. As a non-limiting example, solvent may be sprayed onto film about to be wrapped on the mandrel as shown in FIG. 4. In some embodiments, the solvent is only partially removed from the polymer film so that the residual solvent acts as a plasticizer. The residual solvent, particularly if it swells the polymer, may enhance fusion between the layers. In some embodiments, the residual solvent is present at a level of 2 weight % to 10 weight % of the polymer, or 5 weight % to 10 weight % of the polymer film.

Another method of processing a polymer that limits or avoids high temperatures and high shear stresses is to use cryogrinding to form small particles of the polymer resin which are subsequently formed into a construct or device.

Cryogrinding is a process in which a material is cooled (typically with liquid nitrogen or liquid argon), and then after cooling, ground or milled into smaller size particles. Cryogrinding is particularly useful for polymers with a glass transition temperature below 25° C. Cryogrinding may reduce the particle size to a number average particle size of in the range of about 0.01 to about 30 microns, preferably in the range of about 0.05 to about 25 microns, and more preferably in the range of about 0.1 to about 10 microns. In some embodiments, the cryoground particles may be utilized in a 3-dimensional "printing" apparatus which is well-known in the art. In some embodiments, the polymer particles may be combined with a fluid (a gas, a liquid, or a supercritical fluid), typically a liquid, which is a non-solvent for the polymer to form a slurry of the polymer in the fluid. The non-solvent may be referred to as a lubricant. The concentration of polymer in the slurry may be from 20 weight % to 70 weight %. As used herein, a "non-solvent" of a polymer is a fluid which dissolves not more than 0.1% of the polymer. The fluid may act as a lubricant to allow processing of the slurry by methods such as extrusion of an unconsolidated tube, or injection molding of an unconsolidated tube or device. The extrusion or injection molding may occur at a temperature in the range of 0 to 25° C. below the melting temperature of the polymer (or 0 to 50° C. above the glass transition temperature, provided it is equal to or greater than 25° C., if the polymer has no melting temperature), and not more than 10° C. above the melting temperature of the polymer (or 10° C. 0 to 75° C. above the glass transition temperature if the polymer has no melting temperature). The non-solvent may be removed (at least 95 weight % or at least 98 weight %) during the extrusion or injection molding process.

As a non-limiting example, the polymer which is cryoground is selected from the group of poly(L-lactide), a copolymer where one constituent monomer is L-lactide, poly(glycolide), a copolymer where one constituent monomer is glycolide, poly(D,L-lactide), a copolymer where the constituent monomers include D-lactide, L-lactide, and at least one member of the group consisting of polydioxanone, poly(4-hydroxybutyrate), and poly(trimethylene carbonate), a copolymer where one constituent monomer is D,L-lactide, polydioxanone, poly(4-hydroxybutyrate), or poly(trimethylene carbonate), a copolymer where at least one constituent monomer is polydioxanone, poly(4-hydroxybutyrate), or poly(trimethylene carbonate), and combinations thereof, and wherein the lubricant (non-solvent) is selected from the group consisting of hydrocarbons, oils or freons.

The unconsolidated tube or unconsolidated device is consolidated by "sintering," or another process. Sintering is a process in which particles are formed into a solid mass by application of heat and pressure but without melting the material. The sintering operation may remove most of the porosity resulting in 0.01% by volume pores. In some embodiments, the consolidation is executed by placing the device or tube under high pressure at a temperature in the range of a lower temperature, the lower temperature being the glass transition temperature of the polymer, a glass transition temperature of the polymer if the polymer exhibits more than one (which may be the lowest, the highest, or an intermediate glass transition temperature), or 30° C. if all glass transition temperatures of the polymer are less than 30° C., and a second higher temperature, where the second, temperature refers to the or a melting temperature, if the polymer exhibits one or more melting temperatures and at least one is 45° C. or greater, or alternatively, if the polymer does not have a melting temperature, a temperature that is not greater than 20° C., 35° C., or 50° C. above the glass transition temperature of the polymer (any one of multiple if multiple exist where one of skill in the art will be able to determine the most appropriate), or if 50° C. above the highest glass transition temperature is less than 45° C., if the melting temperature is less than 45° C., or both, then 45° C. In some embodiments, the unconsolidated tube or unconsolidated device is consolidated by the application of heat and pressure in which the polymer is partially, or completely, melted.

As described above, solvent based methods allow for polymer processing at lower temperatures, and thus, with lower levels of polymer degradation. The drawback to solvent processing is that the solvents may need to be substantially removed prior to packaging the device. Particularly for solvents that the International Council on Harmonization (ICH) classifies as "Class I" or "Class II" solvents, there may be a very low limit of solvent allowed in a medical device product. Class I solvents have unacceptable toxicities and Class II solvents, although less toxic than Class I, may be limited to reduce the potential of adverse events in patients. In addition, residual solvent may act as a plasticizer in the polymer of the device and may impact mechanical strength. Residual solvent may migrate by diffusion to a coating on the device, to other parts of the assembled product, such as, without limitation, to the catheter, balloon, packaging, or a combination thereof, for a stent that is crimped onto the balloon of a vascular catheter and packaged. Thus, it is desirable to remove solvent to a low level such as 2500 ppm (parts per million by weight) or lower, 1000 ppm or lower, or even 100 ppm or lower.

The various embodiments of the present invention encompass methods of removing the residual solvent from the polymer prior to packaging the stent, and in some embodiments, prior to the application of a coating to the stent, such as a coating including a drug. In some embodiments, the removal comprises heating the polymer to and maintaining the temperature at a temperature between the glass transition temperature (or at least 28° C. if the glass transition temperature is lower than 25° C.) and an upper temperature ("heating and maintaining operation"). In some embodiments, the minimum temperature of the "heating and maintaining operation" is at least 30° C. or at least 32° C. As used herein, the term "an upper temperature" when used in the context of the phrase "the glass transition temperature and an upper temperature" refers to the melting temperature, if the polymer exhibits one or more melting temperatures and at least one is not less than 45° C., or alternatively, if the polymer does not have a melting temperature, a temperature that is not greater than 20° C., 35° C., or 50° C. above the glass transition temperature of the polymer, or 45° C., if 50° C. above the glass transition temperature of the polymer is less than 45° C., the melting temperature is less than 45° C., or both. One of skill in the art will be able to determine the appropriate glass transition temperature and melting temperature if the polymer exhibits more than one glass transition temperature, more than one melting temperature, or both. The heating and maintaining operation may be a separate operation from additional processing operations, such as radial expansion, axial expansion, or both, even if the temperature is the same (or within ±5° C.) or within the same range (between the glass transition temperature and an upper temperature). Thus, the heating and maintaining operation is executed in addition to, and after the completion of, the subsequent processing operation in which the polymer is heated to a temperature between the glass transition temperature and an upper temperature. In some embodiments, the temperature of the heating and maintaining operation is between 10° C. above the glass transition temperature and 10° C. below the melting temperature, if the polymer has a melting temperature, or between 15° C. above the glass transition temperature and 15° C. below the melting temperature, if the polymer has a melting temperature and there is more than 30° C. between the glass transition temperature and the melting temperature. If the polymer has no melting temperature, the temperature of the heating and maintaining temperature may be between 10° C. and 45° C. above the glass transition temperature, or between 15° C. and 40° C. above the glass transition temperature (provided that the glass transition and melting temperatures are greater than 25° C. and 40° C., respectively). The temperature of the heating and maintaining operation may fluctuate.

In some embodiments, at least 80 weight %, at least 85 weight %, at least 90 weight %, at least 95 weight %, at least 97 weight %, at least 98 weight %, at least 99 weight %, or at least 99.5 weight % of the residual solvent is removed during the execution of a subsequent processing operation such as, without limitation, radial expansion. In some embodiments not more than 20 weight %, not more than 15 weight %, or not more than 10 weight % of the solvent is removed during the subsequent processing operation. The residual solvent may act as a plasticizer, and the plasticization may allow processing at a lower temperature. In some embodiments, after the execution of the subsequent processing operation, the polymer may include at least 60 weight %, at least 70%, at least 80 weight %, at least 90 weight %, at least 95%, 98 weight %, or 99 weight % of the residual solvent that was in the polymer at the initiation of the subsequent processing operation. The remaining residual solvent may be removed (or at least 90 weight %, at least 95 weight %, or at least 98 weight % of the remaining residual solvent) after the execution of the subsequent processing operation, but prior to additional processing operations, such as coating with a drug coating, packaging, and sterilization, if any are executed. Residual solvent may be removed to an acceptable level prior to initiation of packaging, or prior to the initiation of a drug coating operation.

In some embodiments, the subsequent processing operation is an annealing operation in which the polymer is heated to and maintained at a temperature between the glass transition temperature (or at least 28° C. if the glass transition temperature is lower than 25° C., preferably at least 30° C. and in some embodiments, at least 32° C.), and an upper temperature. Annealing processes are typically performed to allow for polymer relaxation, removal of residual stress from processing, or both. In some embodiments, the solvent is removed during the annealing process, that is at least 80 weight %, at least 85 weight %, at least 90 weight %, at least 98 weight % or at least 99 weight %, and up to 99.9999 weight % of the remaining residual solvent is removed. In some embodiments, the duration of the annealing process is extended beyond the time frame for polymer relaxation, etc. to allow for solvent removal. In some embodiments, the duration may be 1.2 times, 1.5 times, 2 times, or 3 times, and in some embodiments, greater than 3 times, longer than would have been required for only annealing.

In some embodiments, the heating and maintaining operation may be performed in a convection oven. In some embodiments, the polymer is in the form of a tube, and there is a flow of a fluid (a gas, a liquid, or a supercritical fluid), such as air or nitrogen, through the tube during the heating and maintaining operation. The flow may be such that the fluid has a velocity of 0.1 to 100 m/sec. The fluid entering the tube and before contacting the tube would be free of, or substantially free of (not more than 2500 ppm by weight or by volume) the solvent.

In some embodiments, the heating and maintaining operation is executed in a vacuum, that is at a pressure below normal atmospheric pressure (760 Torr±100 Torr, preferably 760 Torr±50 Torr). In some embodiments, the pressure may be at least 0.001 Torr, and not more than 400 Torr, not more than 300 Torr, not more than 200 Torr, or more than 100 Torr, or not more than 50 Torr, but at least 0.001 Torr. The pressure may fluctuate. The operation may be executed in a vacuum oven.

In some embodiments, the heating and maintaining, at any of the above temperature ranges, is executed in an atmosphere with water vapor present, that is in a high humidity environment. The high humidity environment may be a relative humidity between 25% and 100%, preferably between 40% and 100%, and more preferably between 65% and 100%. In some embodiments, the high humidity environment has a relative humidity between 80% and 100%. To maintain the high humidity environment a container of water may be placed in the environment of the polymer (such as, without limitation, an oven). Alternatively, or additionally, there may be a stream of water flowing in the environment of the polymer. The water, whether in a container or flowing, may also absorb the solvent. The high humidity environment may be at normal atmospheric pressure (760 Torr±100 Torr, preferably 760 Torr±50 Torr) or in a vacuum (for example, without limitation, not more than 380 Torr or not more than 200 Torr, but at least 0.001 Torr) as discussed above. Water may plasticize the polymer, allowing for easier removal of the solvent. As a non-limiting example, poly(L-lactide) absorbs up to about 0.6-0.7 weight % water, and poly(D,L-lactide-co-L-lactide) absorbs up to about 1.1 weight % water. For both polymers, water acts as a plasticizer. In some embodiments, the heating and maintaining operation is performed at a temperature below the polymer's glass transition temperature, but not less than 28° C. In some embodiments, the heating and maintaining operation is performed at a temperature of at least 30° C., but below the polymer's glass transition temperature (provided that the polymer has a glass transition temperature of at least 31° C.).

After most of the solvent has been removed (the solvent removal is at least 80% complete, where complete when the specification limit of the solvent is reached, preferably at least 90% complete, and more preferably at least 95% complete), the water may be removed (at least to the specification limits for the polymer, such as but not limited to 0.1 weight %) by another heating and maintaining operation in which the stent is placed in an environment in which the humidity level is lower than the humidity of the high humidity environment, and preferably an environment where the humidity is equal to or less than 40% rh, preferably equal to or less than 30% rh, and more preferably equal to or less than 20% rh, and at least 0.001% rh. The duration of time of the operation in a low humidity environment may be different that the duration of the operation in a high humidity environment. In some embodiments, the water is removed by directing a flow of a fluid (in other words, blowing), such as dry air or nitrogen (less than 2500 ppm water by volume, or by weight), over, around, inside, through, adjacent to, or a combination thereof, the polymer. For example, if the polymer is a tube, air may be blown through, around, or both through and around the tube. The fluid may be at a temperature in the range of 30° C., to the polymer's glass transition temperature (the polymer's glass transition temperature being the lowest glass transition temperature that is also above 30° C. if the polymer has multiple glass transition temperatures), or to 75° C., whichever is lower. In some embodiments, the fluid is heated to the glass transition temperature of the polymer (the polymer's glass transition temperature being the lowest glass transition temperature that is also above 30° C. if the polymer has multiple glass transition temperatures) or just above the glass transition temperature (within 10° C. of the polymer's glass transition temperature), provided that the polymer has a least one glass transition temperature at or above 30° C.

In some embodiments, the heating and maintaining may be executed in an environment of solvent vapor (removal solvent), where the solvent is not water, but may be a blend of water and another solvent. As used herein, with reference to placing a polymer in an atmosphere of a solvent vapor, a solvent will refer to a substance, including a fluid, that plasticizes, swells, or both plasticizes and swells the polymer. Solvents may be used individually or in combination as the removal solvent. The plasticization, swelling, or both, of the polymer allows for easier removal of the residual solvent. Thus, even if the polymer is exposed to another solvent, the removal solvent, which may also need to be eventually removed, it may be advantageous to use another solvent if it has a lower boiling point and thus would be removed more easily, if it is a lower health hazard, if it is a better plasticizer for the polymer (where a "better" plasticizer lowers the glass transition more at the same weight % of plasticizer), or any combination thereof. In some embodiments, the removal solvent is an ICH class III solvent. As used herein, an "ICH class III solvent" is a solvent that the International Council on Harmonization has classified as less toxic than class I or II solvents and is recommended for use in production of drugs, excipients, and medicinal products instead of Class I and Class II solvents. In some embodiments, the removal solvent chosen would be a good solvent for the polymer where a "good" solvent is a solvent in which polymer-solvent interactions are stronger than polymer-polymer interactions or solvent-solvent interactions.

In some embodiments, the removal solvent partial pressure is between 30 Torr and 500 Torr. In some embodiments, the removal solvent partial pressure is not less than 100 Torr. In some embodiments, the removal solvent partial pressure is at least 25% of the vapor pressure of the pure solvent, preferably at least 50%, and more preferably at least 75% of vapor pressure of the pure solvent, and may be up to the vapor pressure of the pure solvent at the temperature of the operation. In some embodiments, the removal solvent is above its boiling point. Preferred removal solvents are those of a relatively low boiling point at atmospheric pressure, that is less than or equal to 80° C., and in some embodiments, less than or equal to 60° C. Some non-limiting examples of solvents that may be useful for the polymer poly(L-lactide), or a copolymer with L-lactide as one of the monomers, include acetonitrile, methanol, ethanol, n-propanol, isopropanol, butanol, fluoroform, freons, methylene chloride ($CH_2Cl_2$), and chloroform ($CHCl_3$). FREON® is the trade name of DuPont for a number of chlorofluorocarbons, chlorofluorohydrocarbons, fluoro-hydrocarbons, and halons. Halons are hydrocarbons in which one or more hydrogen atoms are replaced with bromine, and other hydrogen atoms with other halogen atoms (fluorine, chlorine, and iodine). FREON® solvents include, HFC134a™, the trade name for 1,1,1,2-tetrafluoroethane ($CF_3CFH_2$), and HFC-227ea™, the trade name for 1,1,1,2,3,3,3-heptafluoropropane ($CF_3CHFCF_3$). HFC-134a has a boiling point of −26° C. HFC-227ea has a boiling point of −16° C. In some embodiments, the removal solvent vapor is of a solvent that may at least partially dissolve the residual solvent (at least 10 g/liter solubility, and preferably at least 100 g/liter solubility). Similarly to the situation with a high humidity environment, a container of removal solvent, a flow of removal solvent, or both, may be present in the environment of the polymer. The removal solvent in the environment of the polymer may absorb the residual solvent, as well as assist in maintaining the removal solvent vapor level in the environment.

The amount of removal solvent absorbed by the polymer may be in the range of 0.01 weight % to 20 weight %, preferably 0.02 weight % to 15 weight %, more preferably 0.1 weight % to 12 weight %, and even more preferably 0.2 weight % to 10 weight %. In some embodiments, amount of removal solvent absorbed by the polymer may be in the range of 0.1% to 8 weight %, 2 weight % to 15 weight %, or 5 weight % to 30 weight %. In some embodiments, a sufficient amount of removal solvent is absorbed to lower the glass transition temperature of the polymer by at least 5° C., by at least 10° C., by at least 15° C., or by at least 20° C., but not more than 75° C. A sufficient amount absorbed may be in the range of 0.01 weight % to 50 weight %. In some embodiments, the amount of removal solvent absorbed by the polymer, in the range of 0.1 weight % to 35 weight %, lowers the glass transition temperature by 5° C. to 50° C., or 10° C. to 40° C. In some embodiments, there may be a combination of residual solvent and absorbed removal solvent which acts as a plasticizer.

In some embodiments, the removal solvent is different from any solvent used in production of the polymer, and different from any solvent used in any post-production processing of the polymer. In some embodiments, the solvent is different from a solvent used in the immediately preceding processing operation. In some embodiments, the removal solvent is different from any one or more members of the group of acetone, trichloroethylene, chloroform, dimethylacetamide, tetrahydrofuran, 2-butanone, dioxane, tetrahydrofuran, and cyclohexanone.

In some embodiments, there is at least 30 seconds, preferably at least 1 minute, and more preferably at least 2 minutes, between the previous operation of processing the polymer and the heating and maintaining operation with removal solvent vapor present. In some embodiments, there is at least 30 minutes between the previous operation of processing the polymer and the heating and maintaining operation with removal solvent vapor present.

After the residual solvent is removed, then the removal solvent may be removed from the polymer. The subsequent removal of the removal solvent may be accomplished by a subsequent heating and maintaining operation where no removal solvent vapor is added to the environment, or is present in the environment. In some embodiments, the polymer is moved to a new environment which is initially free of, or substantially free of (<2500 ppm by weight or volume), the removal solvent vapor. In some environments, there is a flow of a fluid such as air or nitrogen around, inside, over, or adjacent to the polymer, and the fluid that flows is initially (prior to contact with the polymer or as provided to the environment of the polymer) free of or substantially free of (<2500 ppm by weight or volume) the removal solvent vapor. However, as the operation is executed there will be removal solvent vapor present in the environment due to the evaporation or diffusion from the polymer. In some embodiments, a subsequent heating and maintaining operation is executed for removal of the removal solvent for a duration of time of not less than 10 minutes, and not more than 24 hours, with the removal solvent partial pressure in the environment being less than 50% of saturation, less than 25% of saturation, or less than 2500 ppm removal solvent vapor. In some embodiments, at least 90 weight %, at least 95 weight %, or at least 98 weight % of the removal solvent absorbed into the polymer during the operation is removed from the polymer. In some embodiments, the residual removal solvent in the polymer after removal of the removal solvent, and in some embodiments, at the initiation of packaging, is not more than 1000 ppm (parts per million by weight), not more than 500 ppm, or not more than 100 ppm.

The duration of a heating and maintaining operation may range from 10 minutes to 240 hours or more, whether performed at normal atmospheric pressure, in a vacuum, in a high humidity environment, in the presence of a removal solvent vapor, or a combination thereof. If the heating and maintaining operation in the absence of a vacuum, a high humidity environment, or the presence of a removal solvent vapor, the duration may be longer than if the execution occurs in the presence of one or more of a vacuum, a high humidity environment, and presence of a removal solvent vapor. In some embodiments, the duration is from 10 minutes to 2 hours, from 30 minutes to 4 hours, from 1 to 10 hours, from 1 to 12 hours, from 2 to 16 hours, from 2 to 24 hours, from 4 to 48 hours, from 12 to 72 hours, or from 24 to 200 hours. In some embodiments, the duration is between 0.2 hours and 1000 hours, 0.5 hours and 1000 hours, or 1 hour and 1000 hours.

In some embodiments, the residual solvent is removed by supercritical fluid extraction. The polymer or polymer construct may be placed in a chamber which is sealed, and then filled with a flow of a fluid at or slightly above (within 5° C.) its critical temperature until the fluid reaches its supercritical pressure, and thus is in a supercritical condition. Once a supercritical condition is reached, a continuous flow of the fluid through the chamber is initiated while maintaining the supercritical conditions. The fluid exiting the chamber goes through a restrictor valve which lowers the pressure converting the fluid to a gas phase, with concomitant condensation of the residual solvent. Non-limiting examples of fluids which may be used in supercritical fluid extraction include carbon dioxide, methane, ethane, and ethylene. The duration of the supercritical extraction may range from 5 to 120 minutes. Carbon dioxide is preferred as the critical temperature is between 31 and 32° C.

In some embodiments, the residual solvent is removed by freeze drying. The advantage of freeze drying is that the polymer is not heated to a high temperature.

The polymers that are described herein for use in the embodiments of the present invention may be used individually or in combination.

In preferred embodiments, the polymer is Poly(L-lactide) (PLLA), a polymer with L-lactide or L-lactic acid as a constituent monomer of at least 30 mol %, preferably, at least 50 mol %, more preferably 60 mol %, and even more preferably at least 70 mol %, and up to 98 mol %, a polymer with L-lactide or L-lactic acid as a constituent monomer of at least 30 mol % and having a glass transition temperature of at least 30° C., preferably at least 33° C., and more preferably at least 37° C., or a combination thereof. In some embodiments, the polymer may be poly(L-lactide-co-glycolide), poly(D,L-lactide-co-L-lactide), or a combination thereof with the L-lactide being at least 60 mol %. Poly(L-lactide) (PLLA) is attractive as a stent material due to its relatively high strength and a rigidity at human body temperature, about 37° C. The glass transition temperature (Tg) of PLLA varies between approximately 50 to 80° C., or more narrowly between 55 and 65° C., depending on crystallinity, microstructure, and molecular weight. Since typically, PLLA has glass transition temperature between about 60 and 65° C. (Medical Plastics and Biomaterials Magazine, March 1998), it remains stiff and rigid at human body temperature. This property facilitates the ability of a stent to maintain a lumen at or near a deployed diameter without significant recoil.

In some embodiments, a semicrystalline polymer may be used. Non-limiting examples include poly(L-lactide) (PLLA), polyglycolide (PGA), polymandelide (PM), polycaprolactone (PCL), poly(trimethylene carbonate) (PTMC), polydioxanone (PDO), poly(4-hydroxy butyrate) (PHB), and poly(butylene succinate) (PBS). A non-limiting exemplary amorphous polymer that may be used as the polymer in the embodiments of the present invention is poly(D,L-lactide) (PDLLA). Additionally, block, random, and alternating copolymers of the above polymers may also be used in embodiments of the present invention, for example, poly(L-lactide-co-glycolide).

Other preferred polymers include, without limitation, those having a glass transition temperature of at least 30° C., preferably at least 33° C., and more preferably at least 37° C., or if multiple glass transitions, the part of the polymer having a glass transition temperature less than 30° C. comprises less than 40 weight % or less than 40 mol % of the polymer, and preferably, less than 30 weight % or less than 30 mol % of the polymer. Other polymers that may be used include, without limitation, poly(glycolide), a copolymer where one constituent monomer is glycolide, poly(DL-lactide), a copolymer where the constituent monomers are D-lactide, L-lactide, and at least one of the group of polydioxanone, poly(4-hydroxybutyrate), and poly(trimethylene carbonate), a copolymer where at least one constituent monomer is polydioxanone, poly(4-hydroxybutyrate), or poly(trimethylene carbonate), and combinations thereof.

In some embodiments, the polymer is has an inherent viscosity of at least 3.3 dl/g in chloroform at 25° C., has a number average molecular weight greater than 250,000 g/mole, has a weight average molecular weight greater than 280,000 g/mole, or a combination thereof. In some embodiments, the polymer has an inherent viscosity of at least 4.0 dl/g, at least 4.5 dl/g, at least 5.0 dl/g, at least 6.0 dl/g, or at least 7.0 dl/g in chloroform at 25° C. For the polymer, the upper limit of inherent viscosity may be 25 dl/g, 15 dl/g, or 10 dl/g in chloroform at 25° C. The polymer may have a number average molecular weight not greater than 1,200,000 g/mole, the polymer may have a weight average molecular weight of not greater than 1,500,000 g/mole, or both. In some embodiments, the polymer has a number average molecular weight greater than 275,000 g/mole, greater than 300,000 g/mole, greater than 350,000 g/mole, greater than 400,000 g/mole, greater than 500,000 g/mole, greater than 600,000 g/mole, or greater than 750,000 g/mole, but not greater than 2,500,000 g/mole. In some embodiments, the polymer has a weight average molecular weight greater than 300,000 g/mole, greater than 350,000 g/mole, greater than 400,000 g/mole, greater than 450,000 g/mole, greater than 500,000 g/mole, greater than 675,000 g/mole, or greater than 800,000 g/mole, but not greater than 3,000,000 g/mole. In some embodiments, a number average molecular weight ($M_n$) or a weight average molecular weight ($M_w$) may be determined by Gel Permeation Chromatography (GPC) using polystyrene standards.

In some embodiments, the stent body is formed of a polymer blended or mixed with an absorbable metal, for example magnesium, or an absorbable glass, such as iron doped absorbable glass. Other additives may also be included in a medical device body.

The stent may further include a coating of one or multiple layers disposed over the body or scaffolding having thickness of about 30 angstroms to 20 microns, preferably 30 angstroms to 10 microns, and more preferably 150 angstroms to 5 microns. The coating may be free of drugs, or may include a drug. In one embodiment, the coating may be a polymer and drug mixture, which may be called a drug reservoir layer. There may be multiple drug reservoir layers. One or more layers may be below the drug reservoir layer, above the drug reservoir layer, or both, and this applies to each drug reservoir layer in the coating. In sum, there be any number of coating layers, each of which may or may not contain a drug. As a non-limiting example, the coating may be poly(D,L-lactide) and the drug may be an antiproliferative, such as and without limitation, everolimus. The coating may include other additives, or it may be additives other than incidental migration or diffusion of other additives in the device body into the coating. Methods of applying coatings to substrates are well-known in the art.

Other drugs may be used in a coating over the device body, within the device body, or a combination thereof. Drugs may be used individually or in combination. Drugs that may be suitable for use in the embodiments of the present invention, depending, of course, on the specific disease being treated, include, without limitation, anti-restenosis, pro- or anti-proliferative, anti-inflammatory, anti-neoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing, and cardioprotective drugs. Some drugs may fall into more than one category.

The term "anti-proliferative" as used herein, refers to a therapeutic agent that works to block the proliferative phase of acute cellular rejection. The anti-proliferative drug may be a natural proteineous substance such as a cytotoxin or a synthetic molecule. Other drugs include, without limitation, anti-proliferative substances such as actinomycin D, and derivatives thereof (manufactured by Sigma-Aldrich 1001 West Saint Paul Avenue, Milwaukee, Wis. 53233; or COSMEGEN™ available from Merck) (synonyms of actinomycin D include dactinomycin, actinomycin IV, actinomycin I1, actinomycin X1, and actinomycin C1), all taxoids such as taxols, docetaxel, paclitaxel, and paclitaxel derivatives, FKBP-12 mediated mTOR inhibitors, and pirfenidone. Other anti-proliferative drugs include rapamycin (sirolimus), everolimus, zotarolimus (ABT-578), biolimus A9, ridaforolimus (formerly deforolimus, and also known as AP23573), tacrolimus, temsirolimus, pimecrolimus, novolimus, myolimus, umirolimus, merilimus, 16-pent-rapamycin, 40-O-(3-hydroxypropyl)rapamycin, 40-O-[2-(2-hydroxyl)ethoxy]ethyl-rapamycin, 40-O-tetrazolylrapamycin, and 40-epi-(N1-tetrazolyl)-rapamycin. Other compounds that may be used as drugs are compounds having the structure of rapamycin but with a substituent at the carbon corresponding to the 42 or 40 carbon (see structure below).

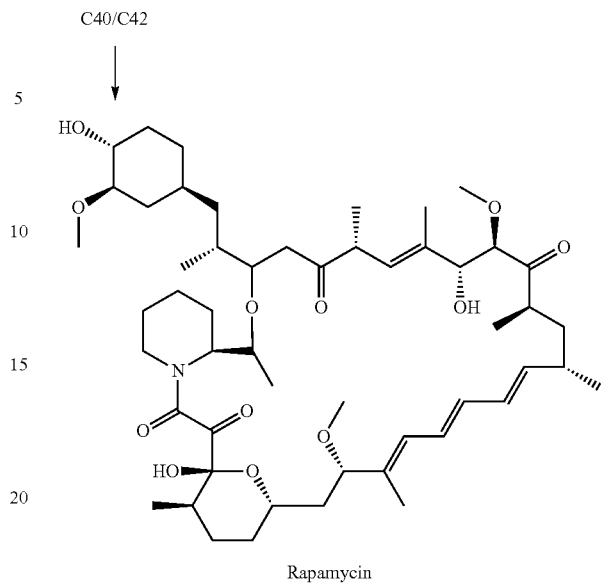

Rapamycin

Additional examples of cytostatic or antiproliferative drugs include, without limitation, angiopeptin, and fibroblast growth factor (FGF) antagonists.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexamethasone phosphate, mometasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Alternatively, the anti-inflammatory drug may be a biological inhibitor of pro-inflammatory signaling molecules. Anti-inflammatory drugs may be bioactive substances including antibodies to such biological inflammatory signaling molecules.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide, nitric oxide donors, super oxide dismutases, super oxide dismutase mimetic and 4-amino-2,2,6,6-tetramethylpiperidine-1-oxyl (4-amino-TEMPO).

Examples of ACE inhibitors include, without limitation, quinapril, perindopril, ramipril, captopril, benazepril, trandolapril, fosinopril, lisinopril, moexipril and enalapril.

Examples of angiotensin II receptor antagonists include, without limitation, irbesartan and losartan.

Other drugs that may be used, include, without limitation, estradiol, 17-beta-estradiol, γ-hiridun, imatinib mesylate, midostaurin, feno fibrate, and feno fibric acid.

Other drugs that have not been specifically listed may also be used. Some drugs may fall into more than one of the above mentioned categories. Prodrugs thereof, co-drugs thereof, and combinations thereof of the above listed drugs are also encompassed in the various embodiments of the present invention.

Representative examples of polymers, oligomers, and materials that may be used, individually or in combination, in the coatings described herein, and optionally, may be used, individually or in combination with any other materials described herein, in forming a medical device body, include, without limitation, polyesters, polyhydroxyalkanoates, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyhydroxybutyrate, polyhydroxybutyrate-co-hydroxyvalerates, polyhydroxybutyrate-co-hydroxyhexanoate, polyorthoesters, polyanhydrides, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(D-lactide-co-caprolactone), poly(D-lactide), poly(glycolide-co-caprolactone), poly(trimethylene carbonate), polyester amides, poly(glycolic acid-co-trimethylene carbonate), poly(amino acid)s, polyphosphazenes, polycarbonates, cellulose acetate, cellulose butyrate, cellulose acetate butyrate, cellophane, cellulose nitrate, cellulose propionate, cellulose ethers, silk-elastin, elastin mimetic peptides, alginic acid, alginate, chondroitin sulfate, chitosan, chitosan sulfate, collagen, fibrin, fibrinogen, cellulose, cellulose sulfate, carboxymethylcellulose, hydroxyl cellulose, hydroxypropyl cellulose, hydroxypropyl methylcellulose (HPMC), carboxymethylcellulose sodium, hydroxyethylcellulose, gelatin, sugars, starch, modified starches, such as hydroxyethyl starch and 2-O-acetyl starches), polysaccharides, dextran sulfate, dextran, dextrin, xanthan, hyaluronic acid, fragments of hyaluronic acid, polysaccharides, and copolymers thereof.

As used herein, the terms poly(D,L-lactide), poly(L-lactide), poly(D,L-lactide-co-glycolide), and poly(L-lactide-co-glycolide) are used interchangeably with the terms poly (D,L-lactic acid), poly(L-lactic acid), poly(D,L-lactic acid-co-glycolic acid), and poly(L-lactic acid-co-glycolic acid), respectively.

As used herein, caprolactone includes, but is not limited to, ε-caprolactone.

For the purposes of the present invention, the following terms and definitions apply:

As used herein, "particle" is a piece of matter held together by physical bonding of molecules, an agglomeration of pieces of matter ("particles") held together by colloidal forces and/or surface forces, a piece of matter which is held together by chemical bonds such as a cross-linked polymer network, a piece of matter formed by ionic interactions, or a piece of matter held together by any combination of agglomeration, surface forces, colloidal forces, ionic interactions, and chemical bonds. For the purposes of this disclosure, a particle will be defined as ranging in size from less than a one tenth of a nanometer to several millimeters in size.

The average diameter of a group of particles depends upon the measurement technique used. In addition, the particular shape of the particles may impact the measured average diameter. For example a sieving method works well for particles that are spherical but for rod-like particles, a sieve representing a particular particle size fraction will retain some rod-like particles while others will pass through as they move through the sieve along the short axis. Thus, the same sized particles may end up on different sieves. Particle diameters may be expressed as a number average particle diameter, a surface area average particle diameter, or a volume average particle diameter. The general formula for the number average diameter for a group of particles is expressed as $d_n = \Sigma_i n_i d_i / \Sigma_i n_i$ where $d_i$ is the diameter assigned to a class of particles, say $d_i = 0.5$ μm for the class of particles from 0 to 1 μm, and $n_i$ represents the number of particles in the category. Using the same classification structure, that is placing the particles in groups and using an appropriate $d_i$ to represent the group, the surface area and volume average diameters are expressed by $d_s = (\Sigma_i n_i d_i^2 / \Sigma_i n_i)^{1/2}$ and $d_v = (\Sigma_i n_i d_i^3 / \Sigma_i n_i)^{1/3}$.

As used herein, if not otherwise specified, the average particle diameter will refer to the diameter determined by dynamic light scattering, that is photon correlation spectroscopy, based on the assumption that the particles observed are spherical, or coulter counting. The average diameter as determined by dynamic light scattering diameters may be the "z average" diameter which represents the mean hydrodynamic diameter. One method for calculating the z-average diameter from dynamic light scattering measurements is provide in the International Standards Organization ("ISO") 13321.

"Compression molding" is a method of molding in which the molding material, generally preheated, is first placed in an open, heated mold cavity. The mold is closed with a top force or plug member, pressure is applied to force the material into contact with all mold areas, and heat and pressure are maintained until the molding material has cured. The process may employ thermosetting resins in a partially cured stage, either in the form of granules, putty-like masses, or preforms. A polymer construct may be formed by compression molding.

"Ram extrusion" refers to a process in which a resin is fed from a hopper and packed into a cylinder in repeated increments by a reciprocating plunger. The frequency and amplitude of the plunger stroke can be controlled by an oil hydraulic system. The compressed material moves through a heated zone where it is fused into a profile matching the cross section of the barrel or die. The output rate is proportional to the length and frequency of the ram strokes. Die length, electrical heater capacity, hydraulic system power and maximum force, and the strength of the construction materials determine equipment capability.

"Gel extrusion", also known as phase separation or extraction or wet process, is a process in which a polymer fluid, including a polymer mixed with a solvent, is extruded. The polymer has a viscosity low enough to be extruded at temperatures below the melting point of the polymer.

As used herein, a "polymer" refers to a molecule comprised of, actually or conceptually, repeating "constitutional units." The constitutional units derive from the reaction of monomers. As a non-limiting example, ethylene ($CH_2$=$CH_2$) is a monomer that can be polymerized to form polyethylene, $CH_3CH_2(CH_2CH_2)_nCH_2CH_3$ (where n is an integer), wherein the constitutional unit is —$CH_2CH_2$—, ethylene having lost the double bond as the result of the polymerization reaction. Although poly(ethylene) is formed by the polymerization of ethylene, it may be conceptually thought of being comprised of the —$CH_2$— repeating unit, and thus conceptually the polymer could be expressed by the formula $CH_3(CH_2)_mCH_3$ where m is an integer, which would be equal to 2n+2 for the equivalent number of ethylene units reacted to form the polymer. A polymer may be derived from the polymerization of two or more different monomers and therefore may comprise two or more different constitutional units. Such polymers are referred to as "copolymers." "Terpolymers" are a subset of "copolymers" in which there are three different constitutional units. The constitutional units themselves can be the product of the reactions of other compounds. Those skilled in the art, given a particular polymer, will readily recognize the constitutional units of that polymer and will equally readily recognize the structure of the monomer or materials from which the constitutional units derive. Polymers may be straight or branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. Polymers may be cross-linked to form a network.

As used herein, a polymer has a chain length of 50 constitutional units or more, and those compounds with a chain length of fewer than 50 constitutional units are referred to as "oligomers." As used to differentiate between oligomers and polymers herein, the constitutional unit will be the smallest unique repeating unit. For example, for poly(lactide) the constitutional unit would be

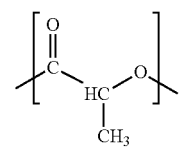

even though the polymer may be formed by the reaction of the cyclic dimer, lactide,

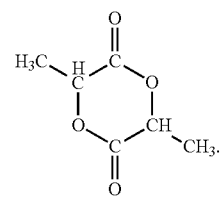

Similarly, for poly(ethylene) the constitutional unit used to count the "number" of constitutional units would be the number of —$CH_2$— units, even though conventionally the constitutional unit is stated to be —$CH_2CH_2$— because it is always derived from the reaction of ethylene.

"Molecular weight" can refer to the molecular weight of individual segments, blocks, or polymer chains. "Molecular weight" can also refer to weight average molecular weight or number average molecular weight of types of segments, blocks, or polymer chains.

The number average molecular weight ($M_n$) is the common, mean, average of the molecular weights of the individual segments, blocks, or polymer chains. It is determined by measuring the molecular weight of N polymer molecules, summing the weights, and dividing by N:

$$M_n = \frac{\sum_i N_i M_i}{\sum_i N_i}$$

where $N_i$ is the number of polymer molecules with molecular weight $M_i$. The weight average molecular weight is given by:

$$M_w = \frac{\sum_i N_i M_i^2}{\sum_i N_i M_i}$$

where $N_i$ is the number of molecules of molecular weight $M_i$. Another commonly used molecular weight average is the viscosity average molecular weight which may be expressed as the following:

$$M_v = \left[\frac{\sum_i M_i^{(1+a)} N_i}{\sum_i M_i N_i}\right]^{1/a}$$

where a is typically less than 1, and is related to intrinsic viscosity.

The "inherent viscosity" (of a polymer) is the ratio of the natural logarithm of the relative viscosity, ηr, to the mass concentration of the polymer, c, i.e. ηinh=(ln ηr)/c, where the relative viscosity (ηr) is the ratio of the viscosity of a polymer solution, η, to the viscosity of the solvent (ηs), ηr=η/ηs.

The "glass transition temperature," $T_g$, is the temperature at which the amorphous domains of a polymer change from a brittle, vitreous state to a solid deformable state (or rubbery state) at a given pressure. In other words, the $T_g$ corresponds to the temperature where the onset of segmental motion in the chains of the polymer occurs. The measured $T_g$ of a given polymer can be dependent on the heating rate and can be influenced by the thermal history, and potentially pressure history, of the polymer, as well as potentially the pressure at which the measurement is made. $T_g$ is also affected by other compounds mixed with the polymer, such as, without limitation, fillers, or residual solvent, etc. The chemical structure of the polymer heavily influences the glass transition by affecting mobility. As used herein the glass transition temperature of the polymer will refer to the glass transition temperature of the polymer as measured by standard differential scanning calorimetry (modulated or unmodulated) with a temperature ramp of 5-20° C./min and if modulated, with a temperature modulation of 0.01 to 2° C. with a modulation period of 1 to 100 seconds, utilizing nitrogen or argon at a flow rate of 10-200 ml/min.

The "melting temperature," $T_m$, of a polymer is the temperature at which an endothermal peak is observed in a DSC measurement, and where at least some of the crystallites begin to become disordered. The measured melting temperature may occur over a temperature range as the size of the crystallites, as well as presence of impurities, plasticizers, or a combination thereof, impacts the measured melting temperature of a polymer.

As used herein, a reference to the crystallinity of a polymer refers to the crystallinity as determined by standard DSC techniques.

Plasticization refers to the addition of a second, lower $T_g$ substance, which is generally lower molecular weight material, to a polymer where the substance is at least partially miscible with the polymer. The effect is to lower the $T_g$ of the blend, and generally, also to transform a hard, brittle material to a soft, rubber-like material. According to the free volume model, the plasticizer, that is the second lower $T_g$ and generally lower molecular weight material, added to the polymer, has a higher free volume. The addition of a higher free volume material to the polymer increases the "free volume" of the blend, and allows for greater polymer chain mobility, thus lowering the $T_g$. An alternative view, based on a lattice model similar to that used by Flory and Huggins, is that the true thermodynamic $T_g$ is the point of zero configurational entropy. Thus, in this model, the lower $T_g$ resulting from the addition of a second smaller molecule is due to the larger number of potential configurations of the polymer chains with the presence of the smaller molecule when compared to the number of potential configurations with only the long chain polymer molecules. Thus, regardless of the theoretical explanation for plasticization, the uptake of a plasticizer would tend to allow for greater polymer chain mobility, and as a result, a lower $T_g$.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional or engineering stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Radial strength" of a stent is defined as the pressure at which a stent experiences irrecoverable deformation. The loss of radial strength is followed by a gradual decline of mechanical integrity.

"Modulus" may be defined as the ratio of a component of stress or force per unit area applied to a material divided by the strain along an axis of applied force that results from the applied force. The modulus is the initial slope of a stress-strain curve, and therefore, determined by the linear hookean region of the curve. For example, a material has a tensile, a compressive, and a shear modulus.

"Strain" refers to the amount of elongation or compression that occurs in a material at a given stress or load, or in other words, the amount of deformation.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material.

As used herein, a "drug" refers to a substance that, when administered in a therapeutically effective amount to a patient suffering from a disease or condition, has a therapeutic beneficial effect on the health and well-being of the patient. A therapeutic beneficial effect on the health and well-being of a patient includes, but is not limited to, any one or more of the following: (1) curing the disease or condition; (2) slowing the progress of the disease or condition; (3) causing the disease or condition to retrogress; (4) alleviating one or more symptoms of the disease or condition.

As used herein, a "drug" also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to, any one or more of the following: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; (3) preventing or delaying recurrence of the disease or condition after a course of treatment with a therapeutically effective amount of a substance, which may be the same as or different from the substance used in a prophylactically effective amount, has concluded.

As used herein, "drug" also refers to pharmaceutically acceptable, pharmacologically active salts, esters, amides, and the like, of those drugs specifically mentioned herein.

As used herein, a material that is described as "disposed over" an indicated substrate refers to, e.g., a coating layer of the material deposited directly or indirectly over at least a portion of the surface of the substrate. Direct depositing means that the coating layer is applied directly to the surface of the substrate. Indirect depositing means that the coating layer is applied to an intervening layer that has been deposited directly or indirectly over the substrate. A coating layer is supported by a surface of the substrate, whether the coating layer is deposited directly, or indirectly, onto the surface of the substrate. The terms "layer" and "coating layer" will be used interchangeably herein. A "layer" or "coating layer" of a given material is a region of that material whose thickness is small compared to both its length and width (e.g., the length and width dimensions may both be at least 5, 10, 20, 50, 100 or more times the thickness dimension in some embodiments). As used herein a layer need not be planar, for example, taking on the contours of an underlying substrate. Coating layers can be discontinuous. As used herein, the term "coating" refers to one or more layers deposited on a substrate. A coating layer may cover all of the substrate or a portion of the substrate, for example a portion of a medical device surface. Typically, a coating layer does not provide a significant fraction of the mechanical support for the device, but a number (including one) of layers of material combined may form a device body, if sufficiently thick, or a device body or substrate may be a multi-laminate structure. In some embodiments, the layers differ from one another in the type of materials in the layer, the proportions of materials in the layer, or both. In some embodiments, a layer may have a concentration gradient of the components. One of skill in the art will be able to differentiate different coating layers or regions from each other based on the disclosure herein.

As used herein, "above" a surface or layer is defined as further from the substrate measured along an axis normal to a surface, or over a surface or layer, but not necessarily in contact with the surface or layer.

As used herein, "below" a surface or layer is defined as closer to the substrate measured along an axis normal to a surface, or under a surface or layer, but not necessarily in contact with the surface or layer.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention. Moreover, although individual aspects or features may have been presented with respect to one embodiment, a recitation of an aspect for one embodiment, or the recitation of an aspect in general, is intended to disclose its use in all embodiments in which that aspect or feature can be incorporated without undue experimentation. Also, embodiments of the present invention specifically encompass embodiments resulting from treating any dependent claim which follows as alternatively written in a multiple dependent form from all prior claims which possess all antecedents referenced in such dependent claim (e.g. each claim depending directly from claim 1 should be alternatively taken as depending from any previous claims).

What is claimed is:

1. A method of making a stent body for supporting a vascular lumen, comprising providing or forming a polymer solution comprising a solvent and a polymer with an inherent viscosity of at least 3.3 dl/g, a number average molecular weight greater than 250,000 g/mole as measured by gel permeation chromatography using polystyrene standards, or both;

either (a) immersing a cylindrical member into the polymer solution and removing the cylindrical member from the polymer solution; wherein a portion of the polymer solution remains on the surface of the cylindrical member upon removal from the polymer solution; and removing at least a portion of the solvent from the polymer solution remaining on the cylindrical member to form a tubular layer of the polymer on the cylindrical member;

or (b) spraying the polymer solution onto the cylindrical member; and substantially removing the solvent during, after, or both during and after the spraying to form a tubular layer of the polymer on the cylindrical member;

optionally, repeating (a) on one or more occasions, repeating (b) on one or more occasions, or both, with repeating of the providing or forming prior to repeating (a), (b), or both, being optional, to form a final tubular layer of polymer on the cylindrical member of a desired thickness, removing residual solvent from the final tubular layer; and forming a stent body from the final tubular layer;

wherein if the optional providing or forming is repeated, for each repetition, the solvent, the polymer, or both, of the polymer solution may be different from the polymer, the solvent, or both used in the prior execution of (a), (b), or both; and wherein removal of the residual solvent from the final tubular layer comprises removal in an environment of solvent vapor, the solvent of the solvent vapor being a removal solvent, where the removal solvent is different from the solvent of the polymer solution; and wherein the removal solvent is selected from the group consisting of acetonitrile, methanol, ethanol, n-propanol, isopropanol, butanol, fluoroform, freons, methylene chloride ($CH_2Cl_2$), and combinations thereof.

2. The method of claim 1, wherein the environment of removal solvent vapor is at a temperature not less than 30° C. but not more than the glass transition temperature of the polymer.

3. The method of claim 1, wherein the environment of removal solvent vapor is at a temperature not less than the glass transition temperature of the polymer, or not less than 28° C., if the glass transition temperature is lower than 25° C., and not more than the melting temperature of the polymer, if the polymer has a melting temperature of at least 45° C., or not more than the higher of 50° C. above the glass transition temperature of the polymer, and 45° C.

4. The method of claim 1, wherein the removal solvent plasticizes the polymer.

5. The method of claim 1, wherein the removal solvent partial pressure is at least 100 Torr.

6. The method of claim 1, wherein the removal solvent partial pressure is at least 50% of the vapor pressure of the pure removal solvent at the temperature of the environment.

7. The method of claim 1, wherein the removal of residual solvent from the final tubular layer in an environment of removal solvent vapor comprises placing the tubular layer in an environment of solvent vapor for at least 0.2 hour and not more than 1,000 hours.

8. The method of claim 1, wherein the environment of removal solvent vapor is at a pressure of 760 Torr±100 Torr.

9. The method of claim 1, wherein the environment of removal solvent vapor is at a pressure of not more than 380 Torr, but at least 0.001 Torr.

10. The method of claim 1, wherein the removal solvent is selected from the group consisting of acetonitrile, methanol, ethanol, n-propanol, isopropanol, butanol, fluoroform, methylene chloride ($CH_2Cl_2$), and combinations thereof.

11. A method of making a stent body for supporting a vascular lumen, comprising:
- coating a web with a polymer solution comprising a solvent and a polymer,
  - wherein the polymer has an inherent viscosity greater than 3.3 dl/g, has a weight average molecular weight greater than 500,000 g/mole, or both;
- removing at least a portion of the solvent from the polymer solution remaining on the web to form a polymer film on the web;
- separating the polymer film from the web; and
- wrapping the polymer film around a cylindrical member, subject to the constraint that the edges of the film at least touch each other, and optionally overlap;
- heating at least part of the polymer film to fuse the polymer film into a polymer tube;
- removing the polymer tube from the cylindrical member; and
- forming a stent body from the polymer tube.

12. The method of claim 11, wherein the wrapping occurs when the polymer film is at a temperature not less than the glass transition temperature of the polymer, and not more than the melting temperature of the polymer, if there is a melting temperature of at least 40° C., or not more than the higher of 50° C. above the glass transition temperature of the polymer and 40° C.

13. The method of claim 11, wherein the wrapping occurs when the polymer film is at a temperature not less than the glass transition temperature of the polymer, and not more than 15° C. above the glass transition temperature of the polymer, or the melting temperature of the polymer, if the polymer exhibits a melting temperature, whichever is lower.

14. The method of claim 11, wherein the polymer film is wrapped around the cylindrical member such that the edges touch each other but do not overlap, or do not overlap by more than 4 times the film thickness.

15. The method of claim 11, wherein heating at least a region of the polymer film comprises heating the edges of the polymer film and the optional overlapping regions of the polymer film to fuse the polymer film to form the polymer tube.

16. The method of claim 11, wherein the polymer film is wrapped around the cylindrical member at least 2 times but not more than 100 times.

17. The method of claim 16, wherein heating at least a region of the polymer film comprises heating all or substantially all of the polymer film to fuse the polymer film to form the polymer tube.

18. The method of claim 17, wherein prior to wrapping the polymer film around the cylindrical member, the polymer film is heated to a temperature, the temperature being at least the glass transition temperature of the polymer, and not more than 15° C. above the glass transition temperature of the polymer, or the melting temperature of the polymer, if the polymer exhibits a melting temperature, whichever is lower;
- wherein after wrapping the polymer film, the polymer film is maintained at the temperature for a duration of time, heated to a higher temperature and maintained at the higher temperature for a second duration of time, or both;
- wherein the higher temperature is not greater than the melting temperature, if there is a melting temperature, or not more than 50° C. above the glass transition temperature of the polymer, if the polymer does not have melting temperature, or 40° C., if 40° C. is greater than 50° C. above the glass transition temperature of the polymer; and
- wherein the first and second durations of time are at least 2 minutes and not more than 120 minutes.

19. The method of claim 17, wherein prior to wrapping the polymer film around the cylindrical member, the polymer film is heated to a temperature being at least the glass transition temperature of the polymer, and not more than 15° C. above the glass transition temperature of the polymer, or the melting temperature of the polymer, if the polymer exhibits a melting temperature, whichever is lower; and is maintained at the temperature for a first duration of time;
- wherein after wrapping the polymer film, the polymer film is heated to a higher temperature, and maintained at the higher temperature for a second duration of time;
- wherein the higher temperature is not greater than the melting temperature, if there is a melting temperature, or at least 50° C. above the glass transition temperature of the polymer, if the polymer does not have a melting temperature, or 40° C., if 40° C. is greater than 50° C. above the glass transition temperature of the polymer;
- wherein the first duration of time is at least 10 seconds and not more than 30 minutes; and
- wherein the second duration of time is not more than 5 minutes, but at least 5 seconds.

20. The method of claim 11, wherein the polymer film is wrapped around the cylindrical member at least 1 full time but less than 2 full times.

21. The method of claim 20, wherein heating at least a region of the polymer film comprises heating at least the overlapping regions of the polymer film to fuse the polymer film to form the polymer tube.

* * * * *